United States Patent [19]
Chisena

[11] Patent Number: 5,171,310
[45] Date of Patent: Dec. 15, 1992

[54] METHOD AND APPARATUS FOR TREATING FRACTURES OF LONG BONES

[76] Inventor: Ernest C. Chisena, 101 Centerport Rd., Centerport, N.Y. 11721

[21] Appl. No.: 704,897

[22] Filed: May 21, 1991

Related U.S. Application Data

[63] Continuation of Ser. No. 381,146, Jul. 17, 1989, abandoned.

[51] Int. Cl.$^5$ .............................. A61F 5/04; A61F 5/30
[52] U.S. Cl. ........................................ 602/5; 602/20; 602/23
[58] Field of Search ................. 128/77, 83, 83.5, 84 C, 128/87 R, 85, 89 R, 157, 165, 160; 606/201, 203; 602/5, 6, 12, 13, 20, 21, 23, 26, 53, 62, 63, 60

[56] References Cited

U.S. PATENT DOCUMENTS

| | | | |
|---|---|---|---|
| 1,404,906 | 1/1922 | Strahl | 128/77 |
| 1,884,927 | 10/1932 | Van Raalte | 128/83 |
| 2,295,253 | 9/1942 | Bloomberg | 128/84 R |
| 2,646,797 | 7/1953 | Scholl | 128/165 |
| 2,655,916 | 10/1953 | Timmins | 602/4 |
| 2,692,594 | 10/1954 | Kelly | 602/21 |
| 2,834,341 | 5/1958 | Stryker | 602/23 |
| 3,074,405 | 1/1963 | Duensing | 128/87 R |
| 3,387,305 | 6/1968 | Shafer | 2/22 |
| 3,575,166 | 4/1971 | Rosman | 602/16 |
| 3,595,225 | 7/1971 | Beeman | 128/77 |
| 3,605,737 | 9/1971 | Berman | 128/165 X |
| 3,788,307 | 1/1974 | Kistner | 128/87 R X |
| 3,934,583 | 1/1976 | Hollingshead et al. | 128/77 X |
| 3,955,565 | 5/1976 | Johnson, Jr. | 602/12 |
| 3,970,081 | 7/1976 | Applegate, Jr. | 128/165 X |
| 4,060,075 | 11/1977 | Blomer et al. | 602/8 |
| 4,070,027 | 1/1978 | Kifferstein et al. | 128/87 R X |
| 4,084,586 | 4/1978 | Hettick | 602/60 |
| 4,130,115 | 12/1978 | Taylor | 602/16 |
| 4,159,020 | 6/1979 | von Soiron | 128/24 R |
| 4,178,922 | 12/1979 | Curlee | 602/19 |
| 4,280,489 | 7/1981 | Johnson, Jr. | 602/27 |
| 4,287,920 | 9/1981 | Johnson, Jr. | 141/85 |
| 4,319,565 | 3/1982 | McMinn | 128/87 R |
| 4,417,570 | 11/1983 | Finnieston | 602/20 |
| 4,470,417 | 9/1984 | Gruber | 128/402 |
| 4,576,153 | 3/1986 | Zagorski et al. | 128/87 R |
| 4,628,918 | 12/1986 | Johnson, Jr. | 602/13 |
| 4,628,945 | 12/1986 | Johnson, Jr. | 128/804 |
| 4,662,364 | 5/1987 | Viegas et al. | 128/87 R |
| 4,697,583 | 10/1987 | Mason et al. | 602/26 |

FOREIGN PATENT DOCUMENTS

| | | |
|---|---|---|
| 2454702 | 5/1976 | Fed. Rep. of Germany . |
| 2808527 | 9/1979 | Fed. Rep. of Germany ...... 128/165 |
| 2936174 | 3/1981 | Fed. Rep. of Germany ...... 128/165 |
| 840438 | 4/1939 | France ................................. 128/165 |
| 2596980 | 10/1987 | France ................................. 128/77 |

OTHER PUBLICATIONS

Viegas, "New Method and Brace for Metacarpal Fractures", Mar. 1987.

Primary Examiner—Robert A. Hafer
Assistant Examiner—Kevin G. Rooney
Attorney, Agent, or Firm—Hoffmann & Baron

[57] ABSTRACT

A method and apparatus are provided for aligning and/or maintaining the reduction of fractures of long bones, to hasten the stimulation of the osteogenesis reaction, the cellular components of fracture healing, and/or the mitigation of pain associated with fractures. In general, the method involves disposing a soft-tissue deforming member in proximity with the fracture of a long bone and applying a radially directed force distribution about the limb and soft-tissue deforming member, to restrict the blood transport through the microcirculation of the soft-tissues, while providing three-point fixation to reduce and maintain angulation of the fracture. As a result of the local restriction of the blood transport through the microcirculation, healing of the fracture is stimulated and pain associated with the fracture is mitigated. In addition, torn blood vessels at the fracture site are physically tamponaded and thereby reduce bleeding from the torn blood vessels. Apparatus for carrying out the method of the present invention, is provided in the form of an orthopaedic device which generally comprises a bracing system and at least one soft-tissue deforming member. The bracing system includes a bracing structure having a longitudinal opening and strapping members for reducing the cross-sectional dimension of the bracing structure, while the soft-tissue deforming member becomes strategically positioned between the bracing structure and the apex of the fracture.

29 Claims, 20 Drawing Sheets $d_2 < d_1$

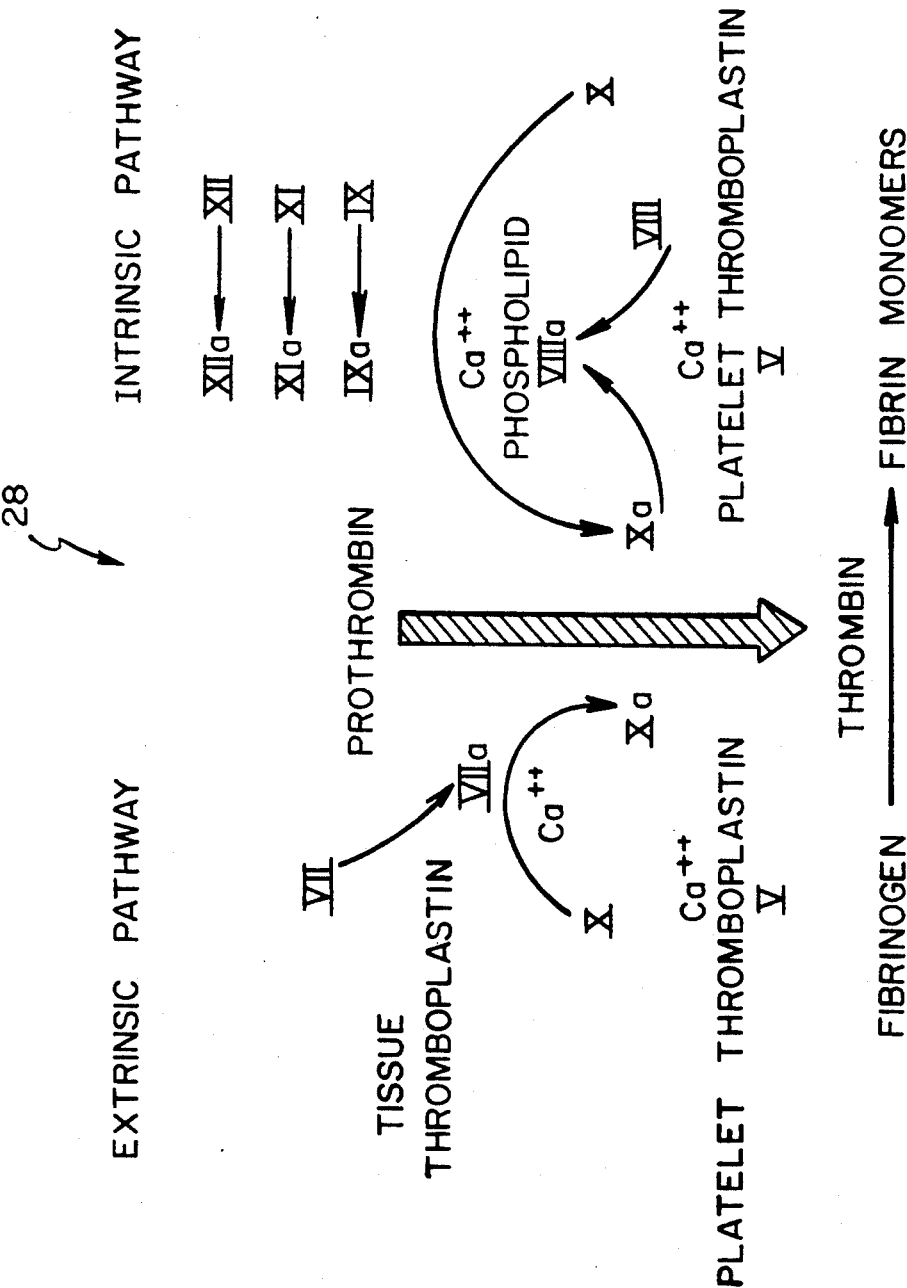

$d_2 < d_1$

METHOD AND APPARATUS FOR TREATING FRACTURES OF LONG BONES

This is a continuation of copending application Ser. No. 07/381,146 filed on Jul. 17, 1989, now abandoned.

BACKGROUND OF THE INVENTION

1. Field of the Invention

The present invention relates generally to orthopaedic methodologies and apparatus for treating fractures of long bones. More particularly, the present invention relates to methodologies and apparatus for aligning and/or maintaining the reduction of fractures of long bones, to hasten the stimulation of the osteogenesis reaction and the cellular components of fracture healing, and/or to mitigate the pain associated with fractures.

2. Description of the Prior Art

Upon fracturing a long bone such as, for example, the humerus, femur, tibia, radius and ulna, several conventional orthopaedic methodologies are available for treating the fracture.

One such methodology involves closed reduction, application of traction through a tibial traction pin with either suspension of the thigh in a splint or cast. In the case of a fractured humerus, such a method involves closed reduction, and immobilization of the fracture using a plaster splint. This method immobilizes the fracture in long bones during a long healing process.

The above-described orthopaedic method, while widely used, nevertheless suffers from numerous shortcomings and drawbacks. Due to the lack of stability provided by plaster of paris splints or casts, the fracture is not stabilized and thus the patient is typically not free to move the extremity about. As a consequence of not moving the extremity about after such treatment, the patient frequently suffers from bedsores or ulcers, and/or pulmonary emboli. With this method, less than perfect reduction of fracture angulation must be accepted. Also, such a methodology typically results in prolonged time periods for healing of the fracture due to the absence of callus proliferation. Moreover, due to the common paucity of callus formation and frequent non-union rate of fractured femurs treated with conventional traction methods, the patient has suffered an enormous amount in terms of pain, discomfort, and the inability to return quickly to the normal activities of everyday life.

There are other prior art methods of treatment, reduction, and immobilization of fractures in long bones, which have attempted to overcome some of the shortcomings and drawbacks of the above described orthopaedic methodologies.

In particular, U.S. Pat. No. 4,576,153 to Zagorski et al. discloses a prior art orthopaedic method which involves the use of a pre-fabricated humeral brace having estimated corrective-surface contours which are permanently fixed at the time of manufacture. This prior art method involves manipulative closed reduction of a fracture, applying traction forces, and thereafter applying the permanently contoured brace about the fractured limb so as to partially correct the remaining angulation of the fractured fragments after closed reduction and traction forces have been applied.

This method, however, also suffers from numerous shortcomings and drawbacks, as well. In particular, since the corrective surface contour of the brace is preset at the time of manufacture, it usually does not provide the appropriate corrective forces to reduce angulation of the fractured bone fragments of a particular fracture. Also, because the plane in which the angulation of the fracture occurs varies greatly, an infinite number of braces must be available to the orthopaedic surgeon to properly treat a patient using this methodology. Moreover, over time, the angulation of the fractured fragments changes, and thus necessitates application of contour braces having different corrective surface contours to further reduce remaining angulation of the fractured fragments. Also, this prior art contoured brace having permanent estimated corrective surface contours, cannot be adjusted in either degree or position, and thus results in the patient having a fracture which heals with less than optimal reduction. Furthermore, using such prior art humeral contour braces, it is difficult, if not impossible, to make adjustments and/or to correct for slight errors in alignment of the surface contours with respect to the fracture. In addition, with this method of fracture treatment, there are no provisions for stimulating fracture healing.

Along similar principles, U.S. Pat. No. 4,662,364 to Viegas et al. discloses an adjustable brace and method for reducing and immobilizing metacarpal fractures of the hand. As disclosed, by providing appropriate pressure to a metacarpal fracture in a desired location, a reduction of fracture angulation and immobilization of the fractured metacarpal can be achieved while allowing movement of the fingers, wrist and hand. The brace includes (i) a C-shaped bracket having a bite portion formed between two generally flat, parallel elongated members, (ii) an apex pad with a pile surface adjustably coupled to one of the flat elongated members, and (iii) a pair of spaced-apart base pads adjustably connected to the other flat elongated member. The flat elongated members have hook material thereon, whereas the apex and base pads have loop material thereon, so that the apex pad and base pads are configurable at a dihedral angle with the hand insertable between the C-shaped member of the bite portion. As disclosed, this allows the pads to be alignable with respect to the fractured metacarpal. A strap is also provided to clamp together the C-shaped bite portion so as to apply pressure from the pads directly against the fractured metacarpal bones, so as to achieve desired reduction and immobilization of the metacarpal fracture.

This method and brace, while having limited use in treating metacarpal fractures, suffers from numerous shortcomings and drawbacks. In particular, the apparatus used in U.S. Pat. No. 4,662,364 cannot be applied to fractures of long bones such as the humerus or femur, and as with prior art pre-contoured braces described hereinabove, the method disclosed therein is limited to applying in a single plane, three-point fixation of pressure to metacarpal bone fractures, and is incapable of reducing or maintaining an angulated fracture of long bones such as the humerus or femur. Furthermore, since the brace disclosed in U.S. Pat. No. 4,662,364 is limited to applying three-point fixation of pressure (to a fractured bone) in a single plane, the brace cannot be used to reduce an angulated fracture, where the apex of the fracture lies beneath and in the same longitudinal plane as the site of a wound or vital structure such as a major nerve or blood vessel. Also because of the flimsy construction and narrow geometry of the strap, the brace cannot possibly control the alignment of a long bone fracture, resist bending loads in any longitudinal plane, or resist any torsional loads. Moreover, U.S. Pat. No. 4,662.364 does not disclose or suggest a way in which to stimulate healing or osteogenesis (i.e. proliferation of callous), as desired in long bone fractures.

Therefore, it is apparent that there is great need in the orthopaedic art for a novel method and apparatus for aligning fractures in long bones, reducing fracture hemorrhage, accelerating the clotting (cascade) reaction, enhancing the cellular components of fracture healing, and stimulating osteogenesis and relieving fracture pain, while overcoming the shortcomings and drawbacks of prior art methods and apparatus.

Accordingly, it is a primary object of the present invention to provide a method and apparatus for carrying out closed reduction of fractures in long bones and stimulating the enchondral osteogenesis reaction by manipulating the biochemical milieu around the fracture, while diminishing the pain associated with the fracture.

A further object of the present invention is to provide an orthopaedic device which, during the first stage of the enchondral osteogenesis reaction, maintains occlusion of the torn blood vessels at the site of the fracture, and by locally increasing the free calcium ion concentration, can accelerate the intrinsic and extrinsic systems of the known coagulation reactions of clot formation.

It is a further object of the present invention to provide such a method and apparatus which, in addition to applying three-point fixation to fractures in long bones, also compresses and deforms the soft-tissues in proximity with the fracture site so as to intentionally inhibit the microcirculation of blood flow in proximity with the fracture site, thereby creating a biochemical milieu which stimulates the enchondral osteogenesis reaction and diminishes the excitability of the free pain nerve endings.

It is a further object of the present invention to provide apparatus for carrying out such a method, in which a biomechanical advantage is provided by the apparatus in order to efficiently achieve restriction in venous and/or arterial microcirculation of the soft-tissues adjacent the fracture.

It is a further object of the present invention to provide such apparatus which is capable of applying in multiple coordinate planes, three-point fixation of pressure to fractures in long bones which are angulated in a particular oblique coordinate plane.

It is a further object of the present invention to provide such apparatus which is capable of easy adjustment in the location of three-point fixation, and the degree of deformation of soft-tissue required during the healing process.

A further object of the present invention is to provide such an orthopaedic device for a fractured femur or humerus which provides immediate pain relief by diminishing the excitability of the free pain nerve endings and a stabilizing effect which gives the patient confidence to allow him to move the fractured extremity about and exercise the same within the first few days after the fracture.

An even further object of the present invention is to provide a method of reducing the angulation of a fracture in a long bone such as the femur or humerus using principles of biomechanical feedback.

An even further object of the present invention is to provide an orthopaedic device capable of providing the most appropriate bracing contour for embracing a fractured long bone so as to maximally control the alignment of the fracture and therewhile stimulate its healing.

Other and further objects of the present invention will be explained hereinafter, and will be more particularly delineated in the appended claims, and other objects of the present invention will be apparent to one with ordinary skill in the art to which the present invention pertains.

SUMMARY OF THE INVENTION

From one of the broader aspects of the present invention, a method is provided for treating fractures in a long bone, to aid in reducing the angulation of the fracture and/or to stimulate healing thereof.

When a bone breaks, the enchondral osteogenesis reaction is initiated and proceeds through four phases: hemostasis, inflammation, organogenesis (i.e. reparative), and finally remodelling. The method and apparatus of the present invention influences the first three phases of the enchondral osteogenesis reaction.

Like other reactions in nature (e.g. chemical and atomic), the geometrical configuration of the components of a reaction, can be arranged to enhance or speed up the reaction. Thus, in a similar manner, the function of the method and apparatus of the present invention is to reposition the fracture components, i.e. the proximal and distal fracture components and the soft-tissues, into a configuration that will maximally enhance the enchondral osteogenesis reaction.

In an effort to develop an effective way to (i) reduce angulation and/or maintain excellent alignment of fractures without surgery and with minimal traction forces, (ii) tamponade torn blood vessels about the fracture site, and (iii) to provide a way in which to stimulate proliferative fracture healing, the applicant has undertaken detailed investigation into the work of others relating to the general effects of vascular restriction on blood microcirculation in soft-tissues, with a view towards achieving these enumerated objectives.

In particular, in the field of plastic surgery, unrelated to fracture healing, plastic surgeons have had a great need to know whether muscle tissue, which has been transplanted, has its appropriate blood microcirculation intact, for tissue viability. In connection therewith, in recent times, a technique of monitoring the pH of the transplanted tissue has been used, in order to provide a measure of the arterial and/or venous microcirculation of transplanted tissue, as it has been long known that with vascular ischemia, there is a rapid decrease in a tissue's pH.

However, studying the work in the area of plastic surgery discussed above, does not provide insight as to how the hereinabove described objects of the present invention may be achieved.

Furthermore, in view of the presently held belief in the scientific community at large, that osteogenesis can be induced or enhanced by an alkalotic environment (i.e. increase in pH), the well known principle that vascular ischemia causes a drop in tissue pH, would be deemed wholly inappropriate in any effort to achieve the objects of the present invention.

Surprisingly, in view of this long held belief of the scientific community, it has been discovered that by locally restricting the venous and/or arterial microcirculation of the soft-tissues about the fracture, several beneficial effects can be achieved, namely:

(i) activating and enhancing the coagulation reactions at the fracture site, thereby hastening the formation of the fracture clot;

(ii) activating and enhancing the facultative anaerobe macrophage, the major cellular component of enchondral fracture healing present at the fracture site;

(iii) stimulating the "mineralization phase" of the enchondral osteogenesis reaction at the fracture site; and (iv) providing a mechanism for mitigating the pain associated with a fracture, to permit the early return of the extremities' functions.

As will be described hereinbelow, the method and apparatus of the present invention utilizes this discovery in part, to provide an effective way of treating fractures of long bones, accompanied by stimulated healing, and a reduction of fracture pain.

In general, the environment for the method of the present invention, will be in a limb or extremity containing an angulated fracture in a long bone which is surrounded by soft-tissues which have a venous and/or arterial microcirculation of blood surrounding the fracture site. In general, the method comprises involves positioning at least one soft-tissue deforming member in proximity with the fracture, and thereafter applying a radially directed force distribution over the soft-tissue deforming member and the skin of the limb about the angulated fracture, such that a stress field is generated in the soft-tissues to establish a three point fixation along the long bone and about the fracture for achieving closed reduction of the angulation thereof. The soft-tissue deforming member imposes a deformation on the soft-tissues, tamponading torn blood vessels, and inhibiting or restricting the venous and/or arterial microcirculation of blood about the fracture. By this method, healing of the fracture is stimulated as a result of intentionally enhancing biochemical reactions associated with the enchondral osteogenesis reaction initiated upon sustaining the fracture.

In general, the intentional local restriction of the venous and arterial microcirculation in the soft-tissues surrounding the fracture, and underlying the soft-tissue deforming member causes a decrease in the pH of the interstitial fluid of these soft-tissues, as well as a decrease in their soluble oxygen concentration. In response, the availability of the free calcium ion is increased, which together with the lowered pH and $P_{O2}$, provides beneficial effects (i), (ii) and (iii) described above.

Another aspect of the present invention is apparatus for carrying out the method of the present invention. This apparatus is in the form of an orthopaedic device for treating fractures in a long bone, to aid in reducing the angulation of the fracture and/or to stimulate the healing thereof. In general, the orthopaedic device comprises a bracing structure, at least one soft-tissue deforming member, and a means for reducing the cross-sectional dimension of the bracing structure.

The bracing structure has interior and exterior surfaces, and a longitudinal opening formed in the bracing structure which allows for easy application of the orthopaedic device to the fractured limb. Also, the bracing structure has a cross-sectional dimension which can be selectively changed, and exhibits a substantial rigidity in the longitudinal direction thereof. In addition, the bracing structure is of a size and shape to encircle the limb containing the angulated fracture in a long bone surrounded by soft-tissues, within which there is a venous and/or arterial microcirculation of blood.

The soft-tissue deforming member has a predetermined three-dimensional geometry and is capable of being detachably disposed on the interior surface of the bracing structure at positions such that, when the bracing structure encircles the limb, the soft-tissue deforming member is disposed in proximity with the fracture site of the long bone. The cross-sectional dimension reduction means of the bracing structure, is provided so as to provide a radially directed force distribution over the soft-tissue deforming member and the skin of the limb and about the angulated fracture, such that a stress field is generated. In turn, the stress field establishes a three point fixation along the long bone about the fracture site for achieving closed reduction of the fracture angulation of the long bone, and the soft-tissue deforming member causes the soft-tissues to be deformed in a manner generally corresponding to their predetermined geometry. This soft-tissue deformation in turn, restricts or inhibits the venous and/or arterial microcirculation of blood about the fracture, whereby healing of the fracture is stimulated.

In the preferred embodiment, the orthopaedic device of the present invention comprises a bracing system and at least one soft-tissue deforming member. The bracing system includes a tongue-shaped structure in addition to the bracing structure. The tongue-shaped structure has interior and exterior surfaces, and is flexibly connected to the bracing structure in order to permit the bracing structure to slide over one side of the tongue-shaped structure. In this manner, the tongue-shaped structure is generally configurable for placement over the longitudinal opening of the bracing structure. As configured, the cross-sectional dimension of the bracing system can be selectively changed in order to create the radially directed force distribution required by the fracture treatment method of the present invention.

In the preferred embodiment, the lengthwise and widthwise dimensions of the soft-tissue deforming member correspond to the major and minor axes of an ellipse, whereas the height-wise dimension diminishes in any direction away from its center, e.g. its curvature along both the major and minor axes is convex. Preferably, the parameter K, defined as the ratio of the height-wise dimension of the soft-tissue deforming member to the diameter of a limb at the fracture, lies in the range of about 0.05 to about 0.25. The parameter K provides a clinically useful measure, from which the orthopaedic surgeon can determine with a reliable degree of accuracy, the height of the soft-tissue deforming member required for carrying out the method of the present invention.

In the preferred embodiment, where the soft-tissue deforming member is formed of a compressible material when subjected to the stress distribution generated by the bracing system hereof, there arises the need to determine the uncompressed height dimension of the soft-tissue deforming member so that the mechanical functions and consequential biochemical responses are obtained by the method and orthopaedic device of the present invention, without causing necrosis to the tissues of the extremity. Accordingly, the method of the present invention also provides a reiterative procedure for determining the height of the soft-tissue deforming member, in which the ratio K is employed.

The method and apparatus of the present invention can also be used to treat fractures in a long bone, to aid in maintaining the non-angulation of the long bone fracture and resisting the contraction of the musculature attached to the long bone, and to stimulate healing of the fracture.

Another aspect of the present invention is to provide a method of mitigating the pain of a patient associated with a fracture in general, and of a long bone in particular. In such situations, the long bone is surrounded by periostial tissue, muscle and fascial tissues all of which have a microcirculation in the tissues and embodying pain sensory receptors including free pain nerve endings. All of these structures are in intimate communication with the interstitial fluid environment of the soft-tissues, which is characterized by a pH and contains elemental minerals including calcium in a bound and free ionic state. The sensory receptors are activatable by various mechanical stimuli and their excitability is responsive to the free calcium ion concentration. Also, the pH of the soft-tissues' interstitial fluid is controlled by the balance between cellular metabolism and blood transport through the microcirculation of those soft-tissues. In view of these biochemical conditions and this metabolic balance, the method of the present invention involves decreasing the pH of the interstitial fluid so as to increase the free calcium ion concentration of the interstitial fluid, which is in intimate communication with the sensory receptors. In response to the increase in the free calcium ion concentration of the interstitial fluid, the excitability of the pain sensory receptors in turn is diminished, whereby the pain of a patient associated with the fracture of a long bone is mitigated. This method of pain relief, is carried out using the orthopaedic device of the present invention, by locally restricting the blood transport through the microcirculation of the tissues, while carrying out the above described methods of treatment. Thus, by providing a mechanism for mitigating the pain associated with a fracture, application of the method and apparatus of the present invention permits early return of the extremities' functions.

In addition to providing the above beneficial effects, the method and apparatus of the present invention are capable of physically tamponading torn blood vessels about the fracture site.

As a result of the present invention, a significant contribution has been made to methodologies for treating long bone fractures and advancing the orthopaedic arts in general.

BRIEF DESCRIPTION OF THE DRAWINGS

For a full understanding of the objects of the present invention, reference is made to the following detailed description of the preferred embodiment which is to be taken in connection with the accompanying drawings, wherein:

FIG. 5C is a schematic representation of the cascade mechanism for blood coagulation indicating that several of these reactions are enhanced by the presence of free ionic calcium $Ca^{++}$;

DETAILED DESCRIPTION OF THE PREFERRED EMBODIMENT

In general, while broader aspects of the method and apparatus of the present invention are intended for aligning and/or maintaining diaphyseal fractures of long bones, such as the humerus and femur, and intentionally altering the biochemical milieu about the fracture to achieve one or more beneficial effects to be described in detail hereinafter, the detailed description of the preferred embodiment will be made with respect to the treatment of a fractured humerus. However, in accordance with the principles of the present invention, it is understood that if sufficient soft-tissue surrounds the fracture to tolerate the application of the stress field generated during the application of the method and the orthopaedic device of the present invention, then, as will become apparent hereinafter, the method and apparatus hereof can be used in connection with the treatment of other fractures in the human skeletal system.

Figure 1:
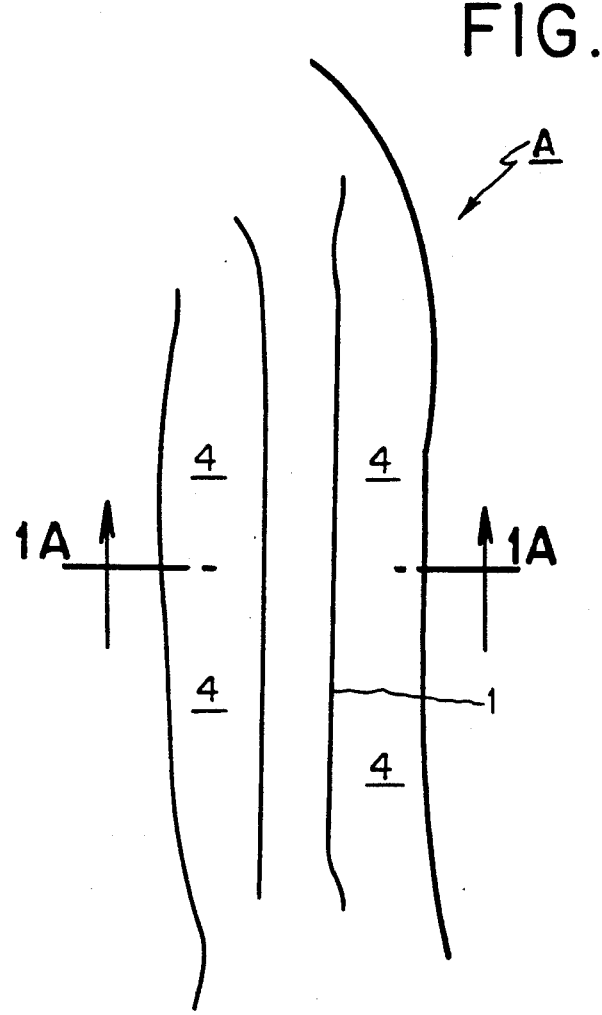
FIG. 1 is a schematic illustration of the arm taken as a longitudinal sectional view, showing the gross relationship between the soft-tissues and the humerus without any fractures.

Referring generally to FIGS. 1, IA, 2, 2A, 3, 3A, 4, 4A, 5A through 5E, 6A through 6C, and 7A through 7C, the method and apparatus of the present invention will now be described with respect to a humerus which has sustained a diaphyseal fracture.

Figure 1A:
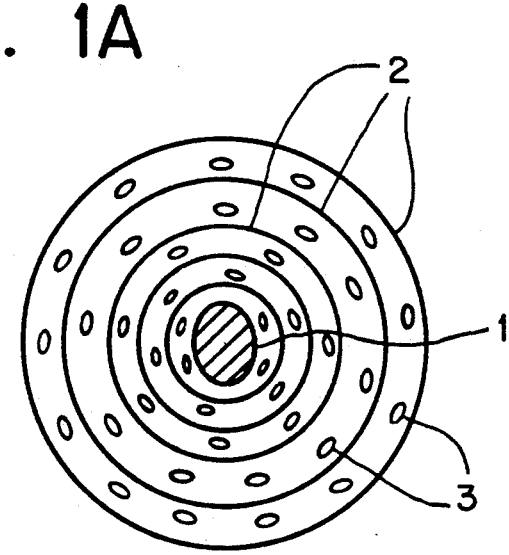
FIG. 1A is a schematic illustration of a cross section of the arm illustrated in FIG. 1 taken along line 1A—1A, showing a substantially uniform distribution of venous and arterial microcirculation represented by substantially open apertures distributed about concentric zones of soft-tissue surrounding the humerus.

As schematically illustrated in FIG. 1, a humerus is surrounded generally by various types of "soft-tissues" which are contained within the outer layers of skin of the arm. As is well known in the medical arts, these soft-tissues may include fat, muscle, fascial tissue, small and large blood vessels, nerves, lymphatic tissue and bone periosteum, but hereinafter will be referred to collectively as "soft-tissues". In FIG. 1A, a cross-sectional view of the arm represented in FIG. 1 is illustrated, taken along line 1A—1A, and schematically represents the layers of soft-tissues about the humerus 1 (i.e. long bone) as concentric rings 2 about the humerus. Each concentric ring 2 contains a plurality of unoccluded apertures 3 or holes representative of venous and/or arterial microcirculation through the soft-tissues residing in the regions generally indicated by reference numeral 4.

Figure 2:
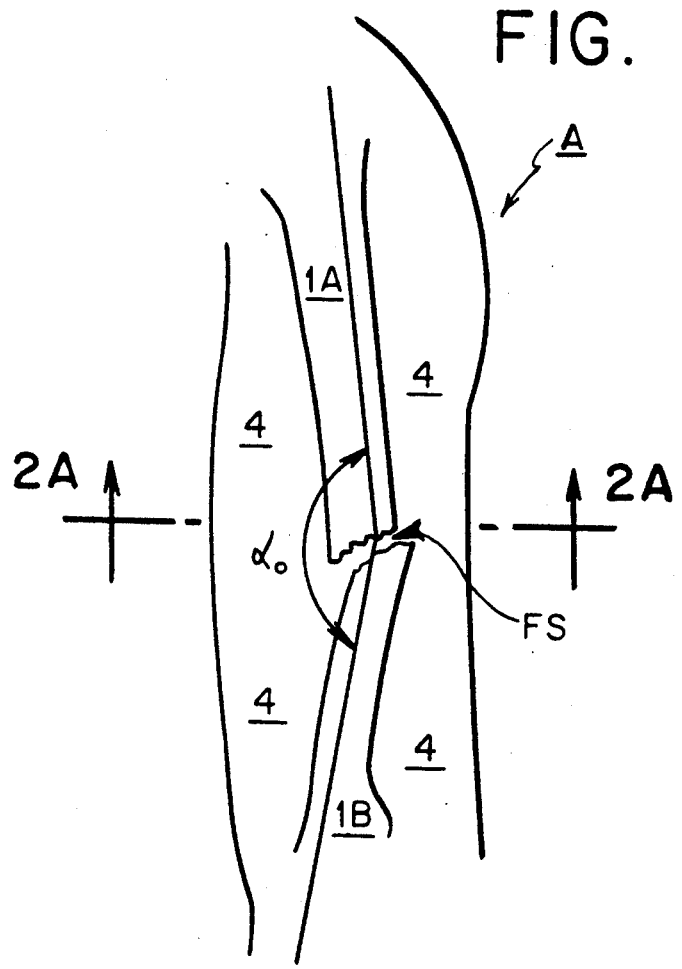
FIG. 2 is a schematic illustration of a longitudinal sectional view in the coronal plane, of the arm showing the gross relationship between the soft-tissues and the humerus with a diaphyseal fracture.
Figure 2A:
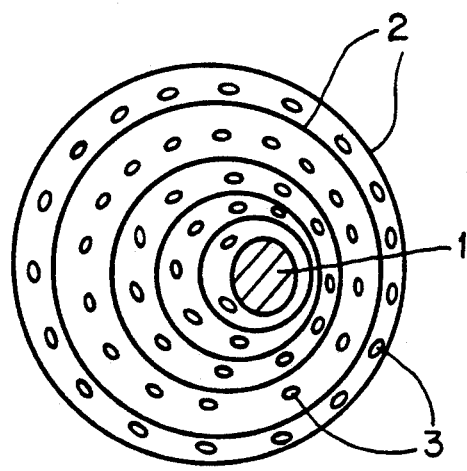
FIG. 2A is a schematic illustration of a cross section of the arm illustrated in FIG. 2 taken along line 2A—2A in proximity with the site of fracture, showing a shift in the position of the humerus with respect to the soft tissues surrounding the same, and a minimally changed distribution of venous and arterial microcirculation surrounding the fracture, represented by substantially open apertures distributed about eccentric zones of soft-tissue surrounding the humerus, with no significant change in the distribution of open blood vessels disposed about the fracture site.

Referring to FIGS. 2 and 2A, a humerus 1 with a diaphyseal fracture is schematically illustrated. As shown, the fractured bone segments 1A and 1B are disposed with respect to each other, with an initial angulation indicated by angle $a_o$. In such a condition, the fractured bone segments are shifted laterally, with the fracture site disposed in the region generally defined by the terminal portions of the fractured bone segments. In FIG. 2A, a cross-sectional view taken along line 2A—2A of FIG. 2 is shown, in which the fractured humerus 1 is shown shifted laterally toward the outer perimeter of the limb. Notably, in such a fractured state, there typically arises a slight distortion of soft-tissue 4, which is schematically indicated in FIG. 2A by the eccentric rings 2 being shown distorted from the condition illustrated in FIG. 1A. It is typically in this condition that an orthopaedic surgeon will receive a fracture in a long bone, and by producing a series of roentgenograms (i.e. X-ray images) using conventional techniques, will confirm this condition in a manner known in the art.

In general, for the case of a diaphyseal fracture in a long bone with initial angulation $a_o$ as shown in FIGS. 2 and 2A, the method and apparatus of the present invention is best described by referring to FIGS. 3, 3A, 4A, 6A, 6B, and 6C, in particular.

Figure 6A:
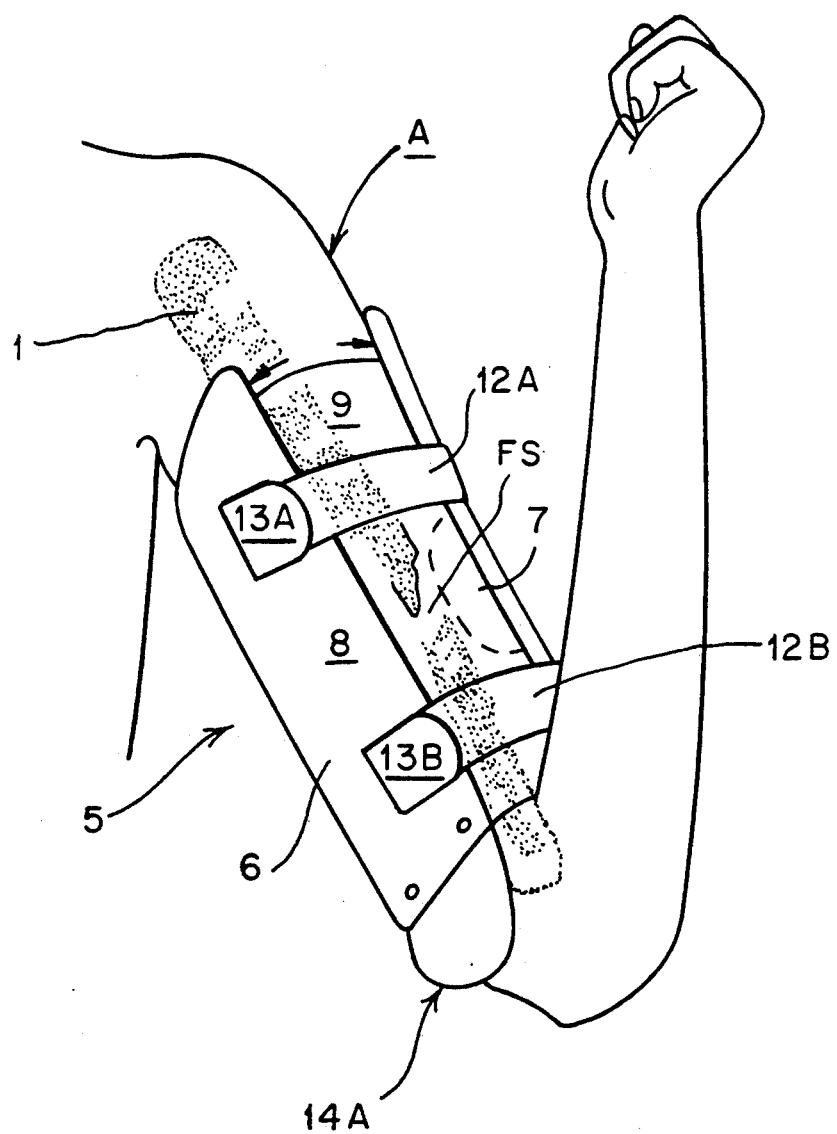
FIG. 6A is a schematic illustration of a perspective view of an arm containing a diaphyseal fracture in the humerus, in which there is shown the bracing system of the device of the present invention, which surrounds the fractured humerus and a soft-tissue deforming member of the bracing system is disposed in close proximity with the apex of the fracture site.

In FIG. 6A, there is shown apparatus of the present invention applied about an arm with a fractured humerus. In the preferred embodiment, the orthopaedic device hereof is in the form of a fracture bracing/soft-tissue deforming system 5 which is more clearly illustrated in FIGS. 6B and 6C.

Figure 6B:
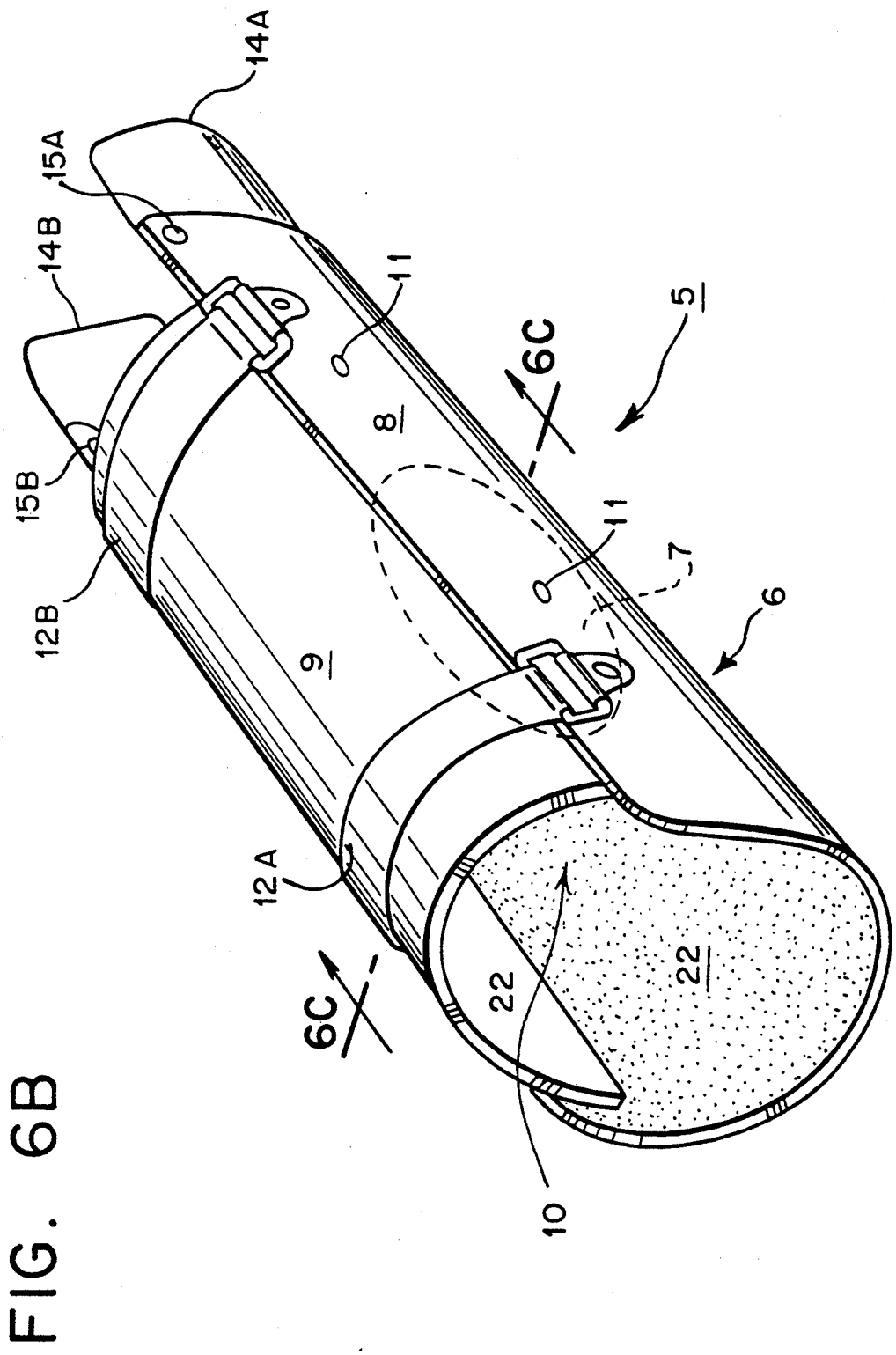
FIG. 6B is a perspective view of the orthopaedic device of the present invention, showing the open substantially-cylindrical support structure, and a tongue-shaped support structure for closing the opening of the substantially-cylindrical support structure when surrounding a patient's fractured limb.

In FIG. 6B, the fracture-bracing/soft-tissue deforming system 5 of the present invention is generally shown comprising a bracing system 6 and a soft-tissue deforming member 7. In general, the bracing system 6 includes a quasi-cylindrical-shaped bracing or support structure 8, a tongue-shaped structure 9, and means 12A and 12B for reducing the cross-sectional dimension of the bracing system 6 (e.g. the bracing structure 8) in order to produce a radial distribution of force over the soft-tissue deforming member 7 and skin of the limb about the fracture.

The bracing structure 8 has a longitudinal opening 10 across which the tongue-shaped structure 9 is disposed by way of rivets 11 as shown in FIG. 6B. This longitudinal opening 10 allows for easy application of the orthopaedic device 5 on the fractured limb. When connected together to the end perimeter edges of the bracing structure 8 along the opening 10, the tongue-shaped structure is free to pivot and tuck under the perimeter edge portion of the bracing structure 8 along the longitudinal opening 10. The structure formed by the bracing and tongue-shaped structures 8 and 9, respectively, is substantially cylindrical and of dimensions so as to fit about and surround the extremity containing the fractured long bone. In general, the bracing and tongue structures 8 and 9 should exhibit substantial rigidity to bending and torsional moments in both the longitudinal and transverse directions of the bracing structure 8, while being flexible in the cross-sectional dimension so that the cross-sectional diameter "d" of the bracing structure 8 can be changed (e.g. reduced) as desired by applying, for example, a hoop stress to the tongue and bracing structure by tightening a pair of strap members 12A and 12B, and fastening their ends 13A and 13B to the exterior surface of the bracing structure 8 using a Velcro(®) fastening system well known in the art. Alternatively, however, a double-walled inflatable structure for surrounding the bracing structure 8 and tongue structure 9, can be used. With such a means surrounding the bracing system 6, pressurized air when introduced into the inflatable structure, will radially expand the walls (closest to the limb) towards the fractured long bone, and thereby reduce the cross-sectional dimension of the bracing system 6, to produce the desired stress field in the soft-tissues.

Figure 6C:
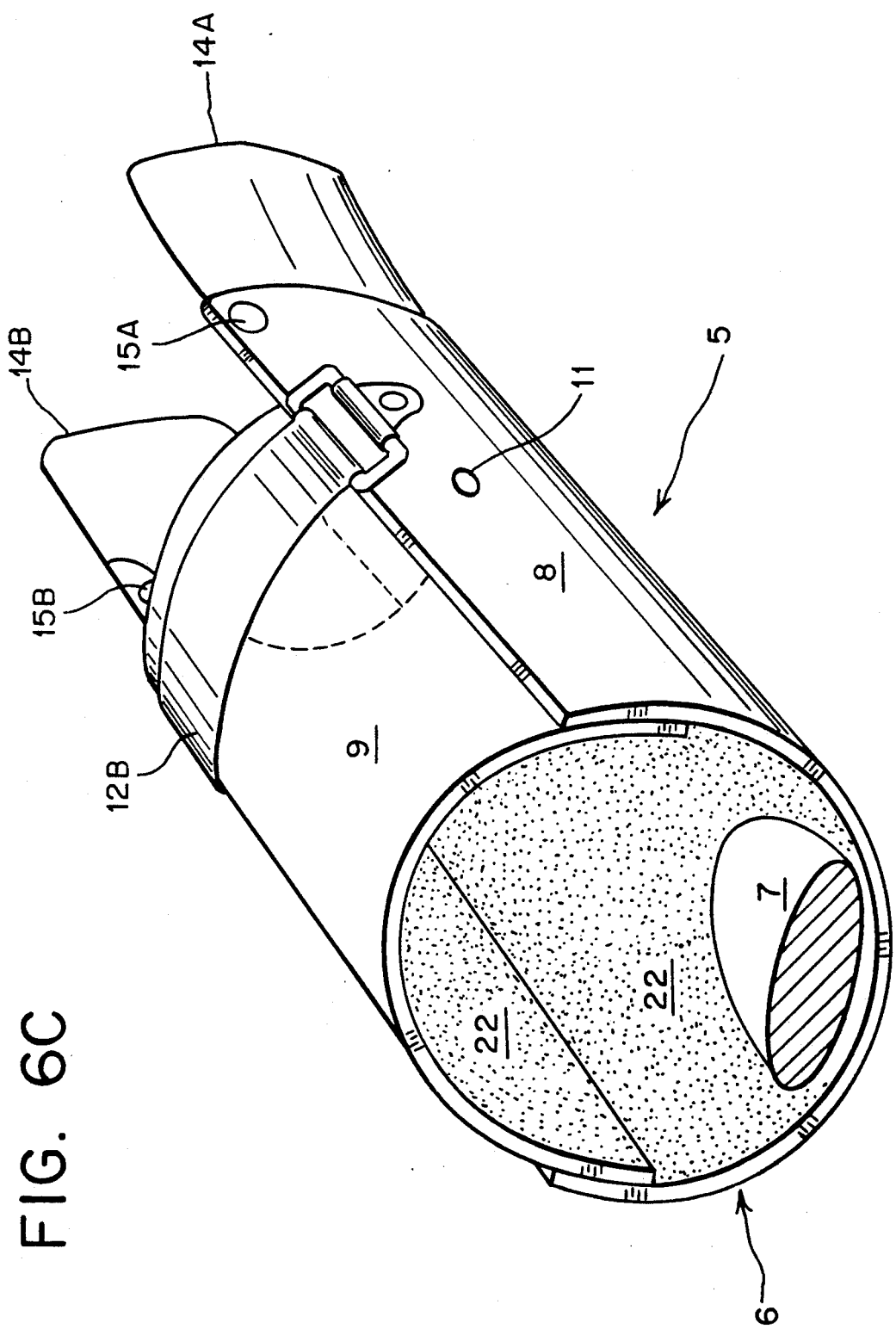
FIG. 6C is a perspective view of the support structure of the orthopaedic device of the present invention taken along line 6C—6C of FIG. 6B, showing a structure disposed on the inner surface thereof for the strategic attachment of the soft-tissue deforming members of the orthopaedic device hereof.

In order to overcome application of torsional moments to the arm, a pair of anti-torsion structures 14A and 14B extend along opposite sides of the bracing structure 8 at the end closest to the elbow as shown in FIG. 6A. These anti-torsion structures 14A and 14B are mounted to opposite sides of the bracing structure 8, by way of rivets 15A and 15B respectively, as shown in FIGS. 6B and 6C. Notably, the soft-tissue deforming member 7 against the deformed soft-tissues and the interior surface of the bracing structure 8 and tongue-shaped structure 9 against the skin of the limb, together create sufficient friction such that the anti-torsion structures 14A and 14B can function. In the preferred embodiment, the bracing structure 8, the tongue-shaped structure 9 and the anti-torsion structures 14A and 14B are made from polypropylene, but other materials having functionally similar properties expectedly can be used as well.

In FIG. 6C, a cross-sectional view of the bracing system 6 and soft-tissue deforming member 7 is shown. In the preferred embodiment, the soft-tissue deforming member 7 has an elliptical geometry in the lengthwise and widthwise dimensions, and has in the heightwise dimension, convex cross-sectional dimensions, i.e. along both its major and minor axes. While the compressed height of the soft-tissue deforming member 7 is an important characteristic of the orthopaedic device 5 hereof, this characteristic and a method for its determination, will be described in greater detail in a later section hereof.

Figure 3:
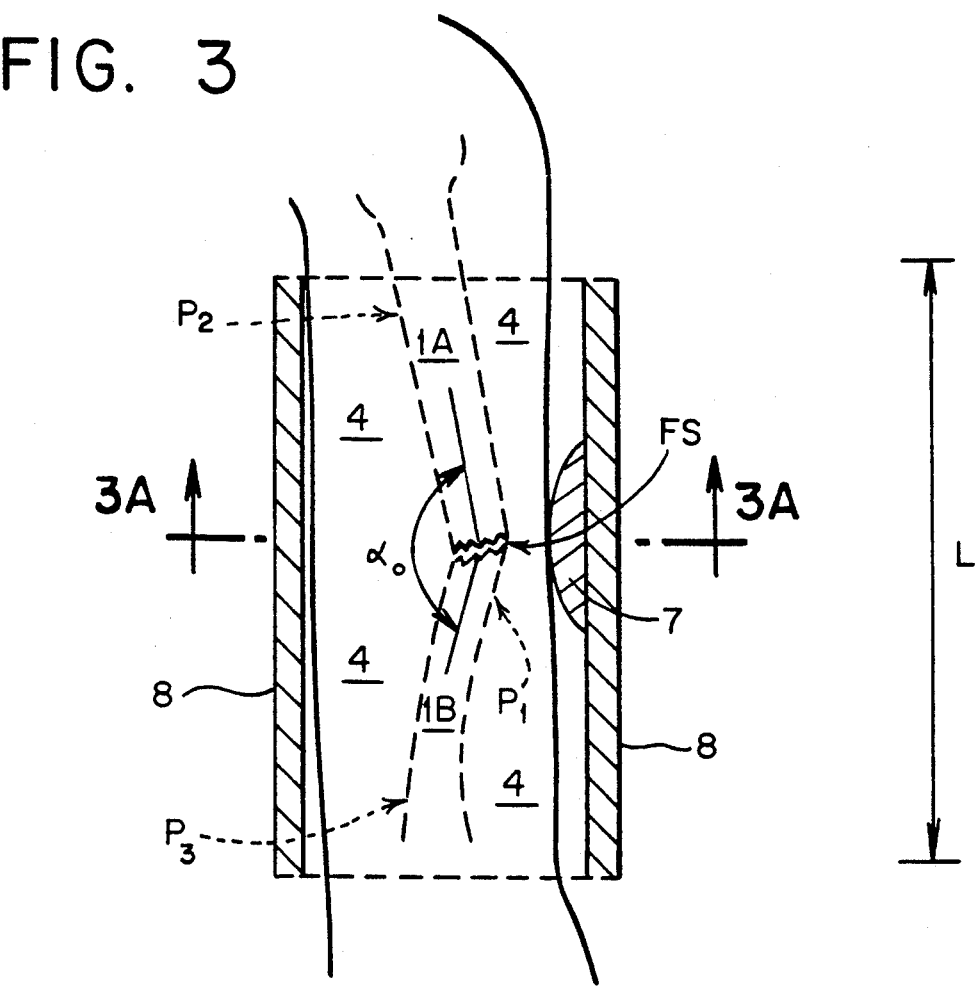
FIG. 3 is a schematic illustration of a longitudinal sectional view in the coronal plane, of the arm showing the humerus with an angulated diaphyseal fracture, with a soft-tissue deforming member of the orthopaedic device hereof disposed just contacting soft-tissues just overlying the apex of the fracture and being surrounded by the substantially-cylindrical bracing structure of the orthopaedic device hereof.
Figure 3A:
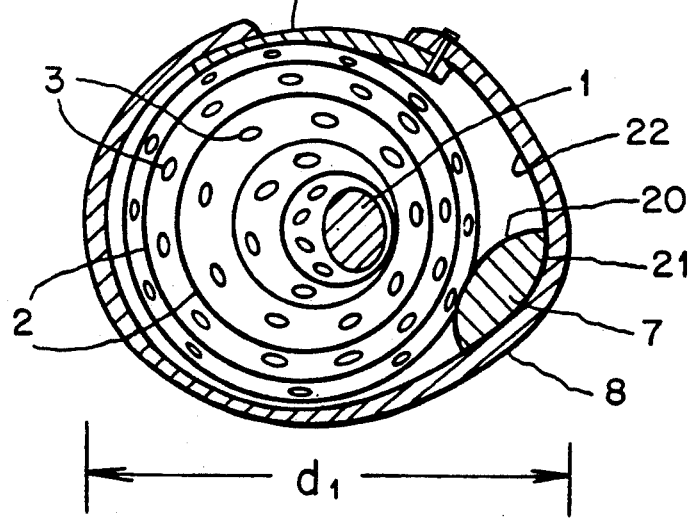
FIG. 3A is a schematic illustration of the cross-section of the arm illustrated in FIG. 3 taken along line 3A—3A, through the fracture site demonstrating no change in the microcirculation of blood flow as schematically represented in FIG. 2A.

Referring now to FIGS. 3 and 3A, the angulated diaphyseal fracture of the humerus illustrated in FIG. 2, is shown with a soft-tissue deforming member or element 7 whose contacting surface 20 is biconvex, disposed in general proximity and overlying the apex of the angulated fracture. FIG. 3 also shows the extremity surrounded by the bracing system 6 hereof, which functions as a means for applying radially directed forces distributed over the non-contacting surface 21 of the soft-tissue deforming member 7 and skin of the limb underlying the bracing and tongue-shaped structures 8 and 9, respectively. The resultant "asymmetrical" stress distribution produced in the soft-tissues by the radially directed forces, can be specified in three-dimensions and is transmitted through the soft-tissues 4 to the shaft of the humerus 1, as will be described further hereinbelow. Preferably, such a three-dimensional "asymmetrical" stress distribution is achieved using the orthopaedic device 5 illustrated in FIGS. 6A through 6C and described above. Notably, the bracing system 6 has a length L relative to the limb and should exhibit an ability to resist bending and torsional moments applied to the limb, and at the same time allow for a decrease in the diameter of its cross section in order to provide (i) the necessary support and produce the "appropriate" asymmetrical stress distribution in the soft-tissues about the fracture during the healing process, and (ii) not produce necrosis of the soft-tissues. Notably, as will be taught hereinafter, this important balance between providing, on the one hand, the necessary support and producing the appropriate asymmetrical stress distribution in the soft-tissues, and on the other hand, not producing necrosis of the soft-tissues, can be reached with the method and apparatus of the present invention.

In FIG. 3A, a cross-sectional view of the bracing system 6 is shown in its "open" or untightened configuration, in which the soft-tissue deforming member 7 is "strategically" positioned on the interior surface 22 of the bracing structure 8. As used hereinafter, the term "strategically positioned" and the like means that the soft-tissue deforming member 7 is positioned at a location o the interior surface 22 of either n the bracing or tongue-shaped structures 8 and 9, respectively, so that when the cross-sectional dimension of the bracing system 6 is reduced, the resulting position of the soft-tissue deforming member overlies the apex of the fracture. In this "open" configuration, the bracing system 5 surrounds the soft-tissues 4 and fractured limb, without yet applying a substantial normal (radial) force distribution. Notably, in this embodiment of the orthopaedic device, the soft-tissue deforming member 7 is disposed at a different location on the interior surface 22 of the bracing structure 8, for purposes of illustration.

In order to "operate" the orthopaedic device 5 of the present invention, the cross-sectional diameter of the bracing system 6 is reduced by applying a hoop stress to the bracing structure 8 and tongue structure 9, i.e. by tightening strapping means 12A and 12B illustrated in FIGS. 6A through 6C. In response to the application of the hoop stress and consequential reduction in diameter of the bracing system 6 (i.e. from $d_1$ to $d_2$ as illustrated in FIGS. 3A and 4A), a distribution of radially directed force is applied over the soft-tissue deforming member 7 and the skin of the limb and about the angulated long bone fracture, so as to achieve both mechanical and biochemical functions through the gross "asymmetrical" deformation of the soft-tissues 4 surrounding the fracture site. The mechanical functions include: the establishment of a fixation of pressure at three points (i.e. "three-point fixation") along the fractured long bone for achieving closed reduction of the angulation thereof; tamponading the torn blood vessels at the fracture site; and local restriction of the microcirculation in the soft-tissues 4 deformed between the soft-tissue deforming member 7 and the apex of the fracture. The "beneficial" biochemical effects obtained through the application of the orthopaedic device 5 of the present invention, will be described hereinafter in detail, and notably, these beneficial biochemical changes in the soft-tissues underlying the soft-tissue deforming member 7, occur secondary to the mechanical functions described above.

In order to carry out mechanical functions described above, the radially directed force distribution provided by the bracing system 6, is transmitted from the soft-tissue deforming member 7, through the soft-tissues, and results in application of pressure along the fractured humerus at three points which are generally indicated in FIG. 3 by $P_1$, $P_2$ and $P_3$, the first, second and third contact points, respectively. Initially, the three pressure points, referred to as "three point fixation," is characterized by three bound force vectors $P_1$, $P_2$, $P_3$ each having a magnitude which is largest at the time when the angulation $\alpha_o$ is largest, and the magnitude tends to decrease over time as the angulation is further reduced, and bone fragments align. In the equilibrium configuration, the magnitude of these force vectors may wax and wane in response to muscle contraction of the soft-tissues.

Figure 4:
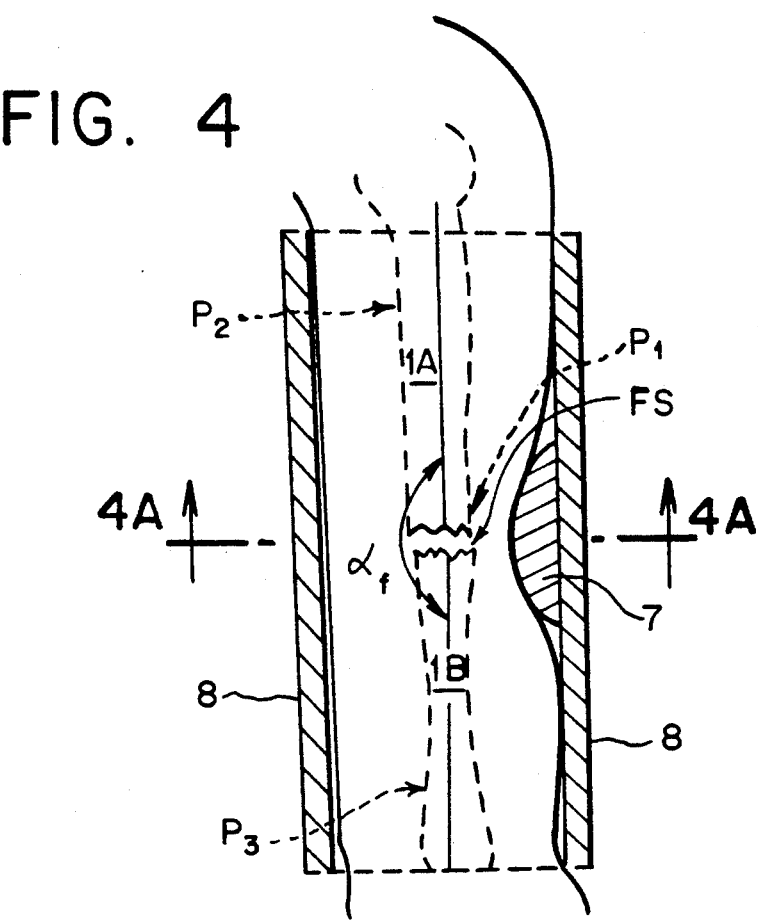
FIG. 4 is a schematic illustration of a longitudinal sectional view in the coronal plane, of the arm of FIG. 3, showing the humerus with a reduction in the angulated fracture, with a soft-tissue deforming member disposed in close proximity with the fracture site and being encircled by the substantially-cylindrical bracing structure of the device hereof, so as to deform the soft-tissues thereabout, transmitting a three-point fixation of normal stress to the fractured humerus to reduce the angulation thereof, and to alter the venous and arterial microcirculation of blood surrounding the fracture site.
Figure 4A:
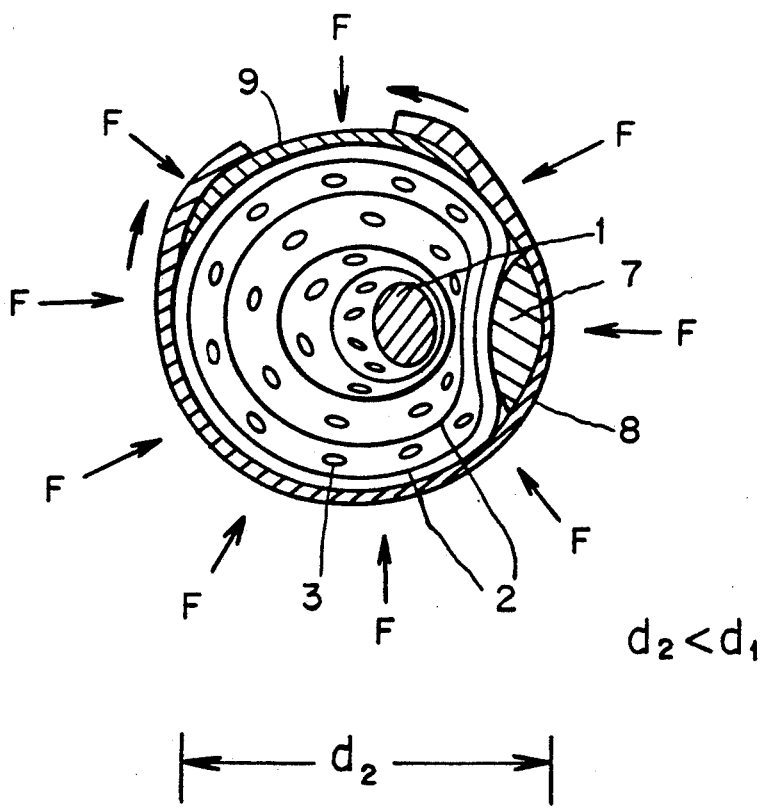
FIG. 4A is a schematic illustration of a cross-sectional view of the arm illustrated in FIG. 4 taken along line 4A—4A through the fracture site, showing a relative shift in the position of the humerus with respect to the soft-tissues surrounding the same, and a grossly altered distribution of venous and arterial microcirculation surrounding the fracture, represented by a decrease in the number of open blood vessel apertures in the region between the soft-tissue deforming member and the fracture.

As illustrated in FIGS. 4 and 4A in particular, when the radially directed distribution of force is applied by the bracing system 6 over the soft-tissue deforming member 7 and the skin of the limb about the angulated long bone fracture, the resulting distribution of stress transmitted through the soft-tissues, not only establishes the three point fixation along the fractured humerus to achieve closed reduction of the angulation thereof, but also achieves (i) tamponading torn blood vessels at the fracture site, and (ii) causes the soft-tissue deforming member 7 to deform the layers of soft-tissue. In turn, this deformation of the soft-tissues locally restricts the venous and/or arterial microcirculation of the soft-tissues locally about the fracture site. This local restriction of the microcirculation of blood about the fracture site is schematically represented in FIG. 4A by the occlusion (or closing off) of the apertures 3 in the rings 2 between the humerus 1 and soft-tissue deforming member 7.

Notably, with the orthopaedic device of the present invention, it is possible to align (i.e. reduce) and maintain an angulated fracture of a long bone with essentially perfect reduction, with minimal traction forces being applied to the limb.

Having described above the method and apparatus of the present invention, attention will now be accorded to the biochemical effects caused by the asymmetrical stress distribution in the soft-tissues described above.

In order to understand the stimulation or enhancement of the healing process at a fracture site, by the mechanical functions and consequential beneficial biochemical effects produced by the orthopaedic device of the present invention, detailed study and investigation into biochemical and mechanical mechanisms have been undertaken, as well as experimentation with regards to apparatus for achieving such mechanisms.

Figure 5A:
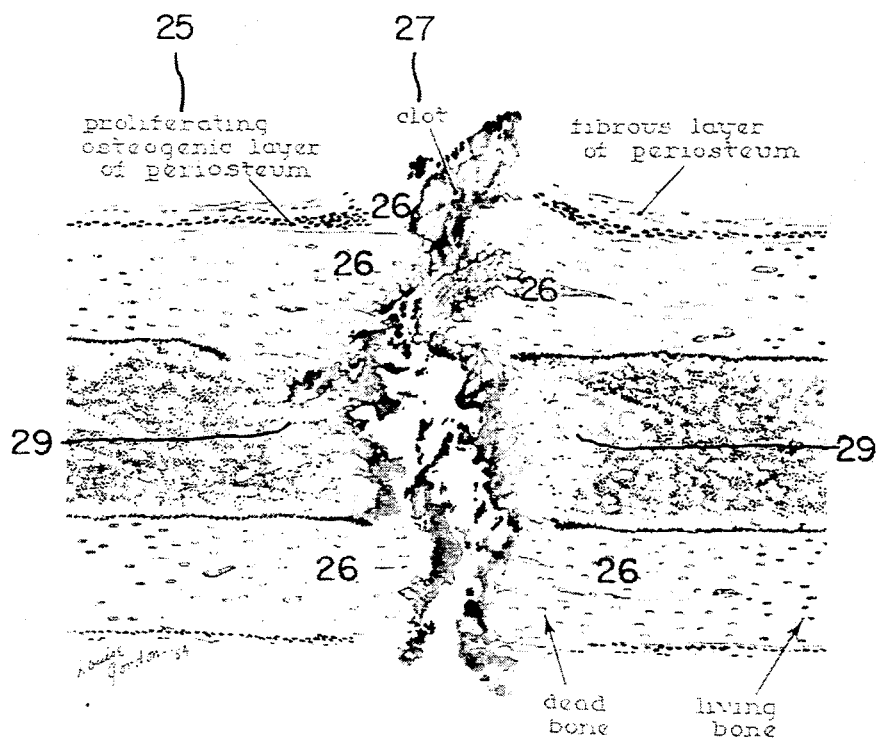
FIG. 5A is a schematic longitudinal cross-sectional illustration of a freshly fractured long bone with the surrounding muscles stripped away, demonstrating the clot formation, the torn sensory receptors (e.g. free nerve endings), and the activated macrophage cell.
Figure 5B:
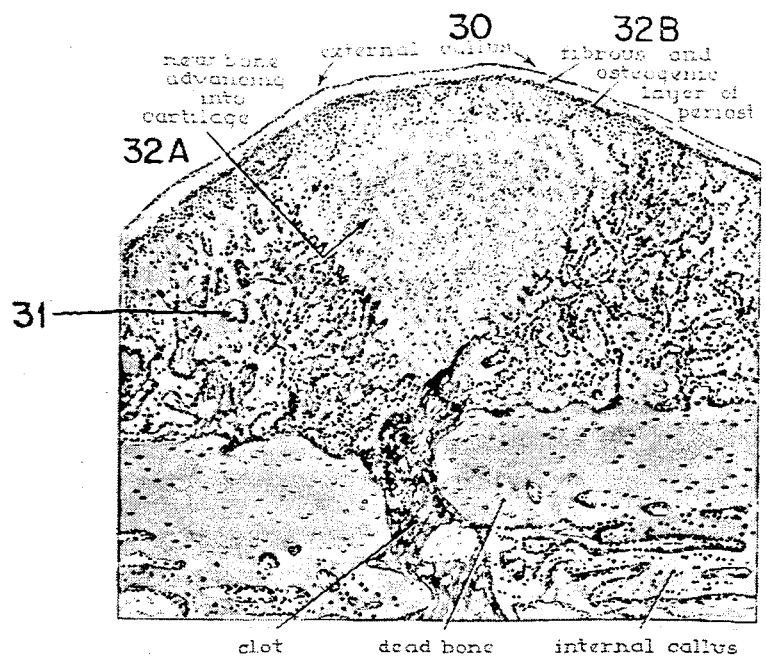
FIG. 5B is a schematic longitudinal cross-sectional illustration of a long bone fracture in a more advanced stage of healing, illustrating the components of the osteoid tissue, including immature fibrous and cartilegous components of the external callous.

Referring to FIGS. 5A and 5B, there is schematically illustrated the first or initial stage in the healing process (i.e. enchondral osteogenesis reaction) of a fracture. As shown, in proximity with the fracture site, there are periosteal tissues 25 and muscles and fascial tissues (stripped away in FIGS. 5A and 5B) which surround the long bone. The periosteal tissues, muscles, and fascial tissues all have a microcirculation including arterial and venous blood vessels of varying caliber, and embody pain sensory receptors including free pain nerve endings 26. It is well known that within the above tissues and even in bone and cartilege, there is an interstitial space among the cells thereof, filled with fluid containing free and bound ions including calcium and other chemical components such as glucose, urea, oxygen ($O_2$) in solution, water ($H_2O$) and carbon dioxide ($CO_2$) in solution. This water ($H_2O$) is in equilibrium with hydrogen ion ($H^+$) and hydroxide ion ($OH^-$). Notably, associated with these and other components constituting the interstitial fluid, there is a resulting hydrogen ion concentration, measured in pH units, where $pH = -\log[H^+]$, with $[H^+] = 10^{-1}$ providing $pH = 1$, and with $[H^+] = 10^{-7}$ providing $pH = 7$.

It is known that the pain associated with a fracture as illustrated in FIGS. 5A and 5B, is transmitted by the peripheral nervous system, whose end sensory receptor is the free pain ending 26. The peripheral nervous system, including the free pain ending, is also known to be exquisitely sensitive to free calcium ion concentration. More specifically, it is known that in general, excitability of the peripheral nervous system is diminished by a high concentration of free calcium ion.

At the instant of fracture, the bone and soft-tissues surrounding the fracture, both of which embody blood vessels and sensory receptors, are torn, resulting in hemorrhage and fracture pain.

During the first stage of fracture healing (i.e. the enchondral osteogenesis reaction), a "clot" 27 forms containing blood cells and blood coagulation factors illustrated in the cascade mechanism 28 for blood coagulation, as shown in FIG. 5C.

It is well known that several reactions within the cascade mechanism 28 are accelerated by an increase in the presence of free calcium ion ($Ca^+$). Examples of such reactions illustrated in FIG. 5C include: $X \rightarrow Xa$; $IX \rightarrow IXa$; prothrombin$\rightarrow$thrombin; etc.

The cellular components present at this first stage of the enchondral osteogenesis reaction in proximity with the fracture site, includes the facultative anaerobe macrophage 29, the major cellular player in fracture healing, which is activated by an anaerobic micro-environment, i.e. low partial oxygen pressure ($P_{O2}$) and low acidity (low pH). The macrophage 29 is the key cell in the initial stages of healing, with a central role in removing the dead tissues about the fracture site and providing nutrients by degrading macromolecules to amino acids and simple sugars.

In FIG. 5B, there is schematically illustrated a portion of the fracture at a latter stage of the enchondral osteogenesis reaction. After the initial stage, in the healing process, the more peripheral portion of the clot 27 and its components have been transformed into the fibrous and cartilageous components of the external callous 30, newly formed bone 31, cartilage 32A and fibrous tissue 32B. These cartilageous components of the external callous are the osteoid 33 which functions as the organic matrix of the about-to-be-formed woven bone, as shown in FIG. 5B. Notably, during the calcium consuming "mineralization phase" of the enchondral osteogenesis reaction, the organic matrix 33 provides a three-dimensional frame or structure into which calcium, present in the surrounding interstitial fluid, is deposited in a rapid calcium consuming reaction.

Reference is now made to FIGS. 5D through 5G in order to describe how, using the principles of the present invention, the intentional alteration of the microcirculation of the soft-tissues surrounding the fracture, as demonstrated in FIGS. 4 and 4A in particular, results in predictable alteration in specific biochemical components (i.e. the hydrogen ion concentration, partial pressure of soluble oxygen and the free calcium ion concentration) in the interstitial fluid of the soft-tissues between the soft-tissue deforming element 7 and the apex of the fracture.

Figure 5D:
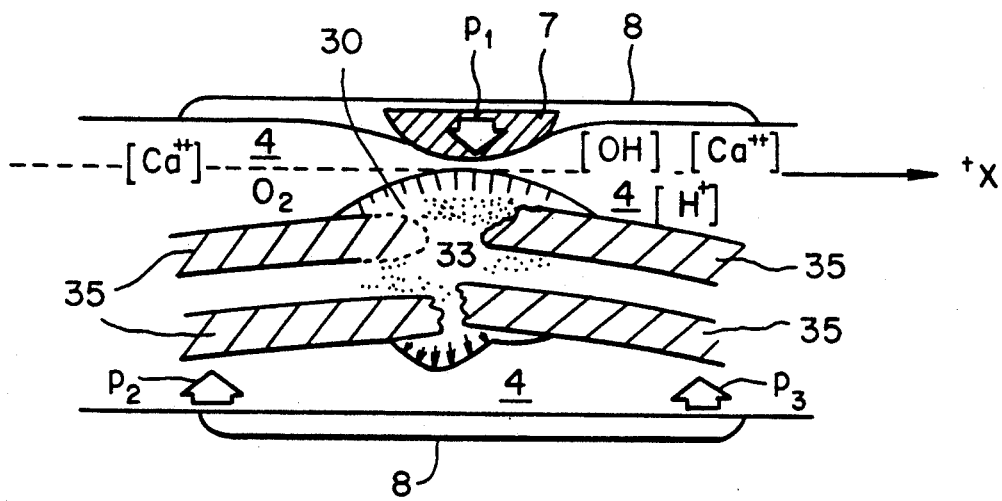
FIG. 5D is a schematic longitudinal cross-sectional illustration of a long bone fracture with a soft tissue deforming member disposed in close proximity with the fracture site and being encircled by the substantially-cylindrical bracing structure of the orthopaedic device hereof, illustrating the alteration of the local oxygen partial pressure (i.e. $P_{O2}$), the local hydrogen and calcium ion concentration (i.e. [pH] and [$Ca^{++}$], respectively) and the close proximity of the fracture osteoid to the altered microenvironment.

In FIG. 5D, there is shown a schematic illustration of a longitudinal cross-section of a fractured long bone about the fracture site, with the bracing system 6 of the present invention applied about the fracture in a manner as described hereinbefore. Specifically, the position of the cortical bone 35 and the major portion of the external callous 30 are illustrated with respect to the soft-tissue deforming member 7 and the bracing structure 8. As shown, the soft-tissue deforming member 7 intentionally restricts the microcirculation of blood flowing through the soft-tissues between the soft-tissue deforming member 7 and the apex of the fracture. It has been discovered that this method of locally restricting in vivo the microcirculation of blood in proximity with the fracture, results in several predictable changes in the above-described biochemical components, namely, the hydrogen ion concentration (pH), partial pressure of soluble oxygen and the free calcium ion concentration [$Ca^{++}$ in the interstitial fluid of the soft-tissues 4.

Figure 5E:
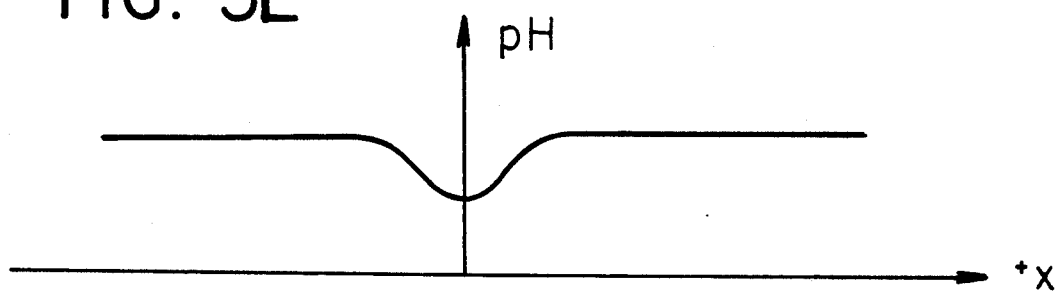
FIG. 5E is a graphical representation of the PH gradient along the x axis shown in FIG. 5D, illustrating a local elevation in the hydrogen ion concentration underlying the apex of the fracture.
Figure 5F:
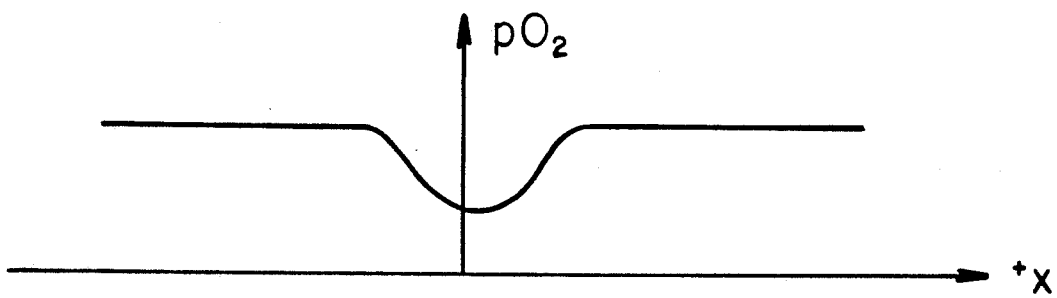
FIG. 5F is a graphical representation of the $P_{O2}$ gradient along the x axis shown in FIG. 5D illustrating a local decrease in the soluble oxygen concentration underlying the apex of the fracture.
Figure 5G:
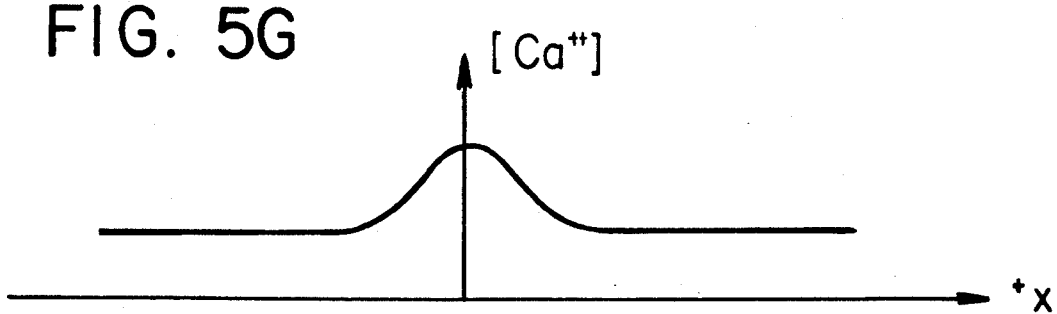
FIG. 5G is a graphical representation of the free calcium ion concentration gradient along the x axis shown in FIG. 5D, illustrating a local elevation in the free calcium ion concentration, caused by a shift in the equilibrium reaction (protein bound calcium→free ionic $Ca^{++}$) in response to a decrease in the local PH achieved by restriction of the microcirculation of the soft tissues overlying the apex of the fracture.

As illustrated in FIGS. 5E and 5F respectively, the concentration gradient of both hydrogen ions (measured by the pH) and the soluble oxygen concentration (measured by the $P_{O2}$) decrease along the region underlying the soft-tissue deforming member 7 where restriction of the microcirculation is greatest. This gradient is defined along the x axis illustrated in FIGS. 5D through 5G.

As a result of the decrease in pH underlying the soft-tissue deforming member 7, the equilibrium between free and bound calcium ion shifts to the free state, that is, increasing the free calcium ion concentration in that same region. This increase in free calcium ion underlying the region below the soft-tissue deforming member 7, in turn, achieves the hereinbefore described "beneficial effects" (i), (iii) and (iv) in accordance with the biochemical mechanisms described below.

As to beneficial effect (i), the increased free calcium ion concentration activates those calcium sensitive reactions in the coagulation mechanism illustrated in FIG. 5C. As to beneficial effect (iii), the increased free calcium ion concentration provides additional calcium for the calcium consuming process of the "mineralization phase" of the enchondral osteogenesis reaction. And, as to beneficial effect (iv), the increased free calcium ion concentration decreases the excitability of the torn free pain nerve endings 26 at the fracture site, thereby mitigating the pain associated with the fracture.

As a result of the lowering of the soluble oxygen concentration ($P_{O2}$) and the pH underlying the soft-tissue deforming member 7, the facultative anaerobe macrophages 29 in proximity of the fracture are activated by the resulting anaerobic (anoxic), acidic microenvironment adjacent to the fracture. This increase in macrophage activity underlying the soft-tissue deforming member 7, in turn, achieves beneficial effect (ii).

Turning now to FIGS. 4, 4A and 6A through 6C in particular, the characteristics of the soft-tissue deforming member 7 of the orthopaedic device 5 hereof and a procedure for determining the same in a particular application, will now be described below.

In accordance with the principles of the present invention, the soft-tissue deforming member 7 of the orthopaedic device hereof must typically have a thickness dimension or height h, in order to ensure that the orthopaedic device 5 hereof carries out its intended functions without causing necrosis of the soft-tissues of the extremity. This height can be "normalized" relative to the diameter d of the extremity at the fracture site to be treated.

A general relationship exists between the "height" h of the soft-tissue deforming member 7 and the diameter d of the extremity, for achieving both the mechanical functions and biochemical "beneficial effects" described hereinbefore. In particular, in order to achieve desired restriction of the microcirculation of the soft-tissues 4, it has been found that a clinically useful measure of this "height" can be formulated as a ratio K, where the ratio K equals the maximally compressed height "$h_c$" of the soft-tissue deforming member 7, divided by the diameter "$d_c$" of the bracing system 6 measured when the extremity is being compressed by the bracing system 6 of the present invention. In order to achieve the beneficial effects of the orthopaedic device hereof and to avoid the problem of tissue necrosis, it has been empirically determined for arms and thighs of a number of patients, that K will typically lie in the range of 0.05 to 0.25. Thus, with this predetermined ratio K (representative of an average value of K), an orthopaedic surgeon can estimate what the initial thickness or height of the soft-tissue deforming member 7 must be for treating a particular extremity. However, this determination may not always be simple and straightforward, as will be explained below.

In the preferred embodiment, the soft-tissue deforming member 7 of the orthopaedic device hereof is preferably formed from a material which yields only slightly under stress, but nevertheless is soft on its outer peripheral surfaces so that comfortable contact between the patient's extremity and the soft-tissue deforming member 7 exists. Thus, a material such as dense Styrofoam (R) can be used, as it can be easily sculptured and has desirable properties, although, a virtually non-compressible material such as wood, plastic or other material properly sculptured can expectedly be used as well.

Notably, however, when using a soft-tissue deforming member 7 which is compressible under typical stress distributions applied thereto by the bracing system 6 (i.e. when tightened down by an applied hoop stress generated by the strapping means 13A/13B), the height of the soft-tissue deforming member 7 when measured in its uncompressed mode, will change (i.e. decrease), as will the compressed diameter of the extremity. Consequently, selection of the thickness of a soft-tissue deforming member 7 for treating a particular extremity, typically will not be attained on the first thickness or height selection. In an effort to minimize the number of steps required to determine the uncompressed "height" or thickness of a soft-tissue deforming member 7 for achieving the functions of the method and orthopaedic device of the present invention, an iterative procedure has been developed. As will be described below, through a series of thickness selection, X-ray imaging, and height measurement and comparison operations, the correct thickness for a soft-tissue deforming member for a particular extremity can be simply and quickly determined, however, the iterative procedure may need to be repeated as the swelling (i.e. diameter) of the extremity recedes, as healing progresses.

The first step of the iterative procedure involves measuring the uncompressed circumference $C_{uc}$ of the extremity (e.g. arm or leg) at the fracture site, and then compute the uncompressed diameter $d_{uc}$ of the extremity at the fracture site, by the geometrical formula:

$$d_{uc} = \frac{C_{uc}}{\pi}$$

Preferably, this conversion can be obtained from a precomputed table for a wide range of uncompressed extremity circumferences.

The subsequent step of the iterative procedure involves using the empirically determined ratio K, to compute a first order approximation of the "uncompressed" height $h_{uc}(1)$ or thickness specification for the soft-tissue deforming member 7. Notably, for purposes of this procedure, the term "height" or "thickness" shall refer to the peak height dimension of the soft-tissue deforming member 7, as illustrated in FIGS. 7B and 7C.

Using the computed uncompressed height specification $h_{uc}(1)$, a soft-tissue deforming member 7 as illustrated in FIGS. 6A through 6C and 7A through 7C is fashioned. Thereafter, the bracing system 6 bearing the fashioned soft-tissue deforming member 7, is applied to the extremity about the fracture site as described hereinbefore.

Then, with the orthopaedic device 5 applied to the extremity in a tightened mode with the soft-tissue deforming member 7 positioned (i.e. located) properly with respect to the fracture, the compressed diameter $d_c(1)$ of the extremity at the fracture site is measured from an X-ray image taken of the extremity with the orthopaedic device 5 applied thereon. Using the compressed diameter parameter $d_c$, the compressed height $h_c(1)$ of the soft-tissue deforming member 7 is computed by the relation:

$$h_c(1) = K \cdot d_c(1)$$

The next step of the iterative procedure involves measuring from the X-ray taken of the extremity with the orthopaedic device 5 in place, the actual compressed height $h_c'$ of the soft-tissue deforming member 7. In rendering the soft-tissue deforming member 7 sufficiently radio-opaque, one of a variety of techniques can be used. For example, the soft-tissue deforming member can be made from or doped with radio-opaque materials, or alternatively, a variety of X-ray imaging techniques can be used to render a soft-tissue deforming member 7 visible.

Then, the calculated height $h_c$ is compared with the actual compressed height $h_c'$, and these values should be of the same magnitude, and at the same time, the fracture alignment should be improving. Notably, subsequent X-rays may justify changes in the height of the soft-tissue deforming member 7. However, the ratio K of compressed height of the soft-tissue deforming member to the compressed diameter of the extremity, will remain essentially constant.

Thereafter, a determination is made as to whether the computed compressed height $h_c$ is greater or less than the actual compressed height $h_c'$ of the soft-tissue deforming member 7. For example, if $h_c > h_c'$, then a thicker soft-tissue deforming member 7 "may be" required. On the other hand, if $h_c < h_c'$, then a thinner soft-tissue deforming member 7 "may be" required. In each instance, reduction of angulation should be considered, and also, whether the patient is experiencing any pain should be ascertained as this could be an indication of ischemia or necrosis of the extremity. The term "may be" is used above because angulation reduction and tissue necrosis considerations "may be" overriding.

If the actual measure of compressed height $h_c'$ is greater than the computed compressed height $h_c'$ (i.e. when the empirically determined value of $K'(1) = h_c(1)/d_c(1)$ is higher than the predetermined value K), then more care must be exercised in order to avoid causing tissue necrosis.

After making the above determinations, either a thicker or thinner soft-tissue deforming member 7 is selected for use in connection with the bracing system 6. This waxing or waning in the height specification can be achieved, for example, by adding or subtracting layers of material to the base portion 21 of the soft-tissue deforming member 7, which are stuck together using a tack adhesive. In this manner, the general geometry of the contact surfaces 20 of the soft-tissue deforming member 7 remain unchanged, while the overall height dimension is changed, as required. Notably, this alteration in the height specification of the soft-tissue deforming member, can be achieved by merely folding back the tongue-shaped structure 9, while the bracing structure 8 remains in position about the extremity (i.e. limb). Thereafter, the orthopaedic device 5 is retightened on the extremity using this second order approximation for the height specification of the soft-tissue deforming member 7. With the orthopaedic device 5 applied to the extremity, another (i.e. second) X-ray is taken and the actual compressed diameter of the extremity $d_c(2)$ at the fracture site is measured therefrom. Then, using the formula $$h_c(2) = K \cdot d_c(2),$$

the compressed height of the soft-tissue deforming member is computed. Thereafter, from the second X-ray, the actual height $h_c'(2)$ of the soft-tissue deforming member is measured, and then compared with the computed height $h_c(2)$ as described hereinbefore. This reiterative procedure is carried out until $h_c'$ converges towards $h_c$ and the angulation reduction is acceptable. Notably, however, X-ray images of the limb taken at a later stage in the healing process, may demonstrate even further reduction of the angulation of the fracture, in response to the continuous application of the orthopaedic device of the present invention.

From empirical data gathered, it has been found that within two or three cycles of the reiterative procedure described above, the actual compressed height $h_c'$ converged towards the computed compressed height $h_c$, with acceptable reduction of fracture angulation being attained.

In order to specify the lengthwise and widthwise dimensions of the soft-tissue deforming member 7, several considerations should be made to ensure effective achievement of the mechanical functions and biochemical effects of the orthopaedic bracing device of the present invention.

In particular, in specifying the lengthwise and widthwise dimenions of the soft-tissue deforming member 7, the orthopaedic surgeon should consider the geometry of the fracture (e.g. traverse versus long spiral). Thus, with the knowledge of both the mechanical and biochemical advantages of the orthopaedic device hereof, the orthopaedic surgeon can select an appropriate lengthwise and widthwise geometry to effectively treat a particular fracture.

In nearly all cases, the minimal widthwise dimension of the soft-tissue deforming member 7 should equal the diameter of the long bone at the fracture site. However, the more oblique the fracture is, the greater the lengthwise dimension of the soft-tissue deforming member 7 must be in order to maximize the beneficial effects of the orthopaedic device of the present invention.

Figure 7A:
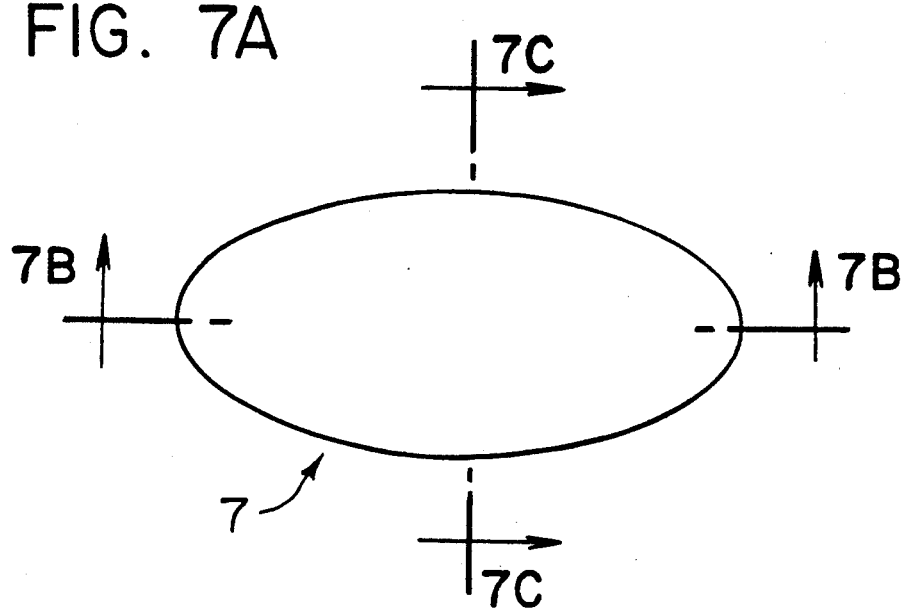
FIG. 7A is a top plan view of a soft-tissue deforming member of the preferred embodiment of the orthopaedic device of the present invention, demonstrating its basically elliptical geometry.
Figure 7B:
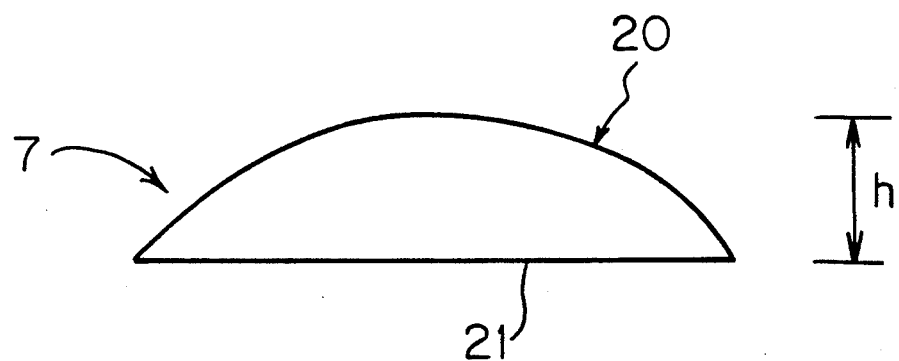
FIG. 7B is an elevated cross-sectional side view taken along line 7B—7B of FIG. 7A, showing the soft-tissue deforming member of the preferred embodiment having a convex deforming surface along that view.
Figure 7C:
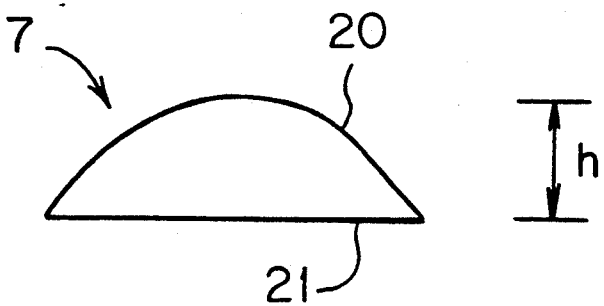
FIG. 7C is an elevated cross-sectional side view taken along line 7C—7C, showing the soft-tissue deforming member of the preferred embodiment having a convex deforming surface along that view.

In the preferred embodiment illustrated in FIGS. 7A through 7C, the soft-tissue deforming member 7 has an elliptical shape in the lengthwise and widthwise dimensions. Here, the major axis of the soft-tissue deforming member 7 is aligned with the longitudinal axis of the extremity (e.g. arm or leg). Also, as illustrated in FIGS. 7B and 7C, the cross-sectional contour of the soft-tissue deforming member 7 is generally "bi-convex". This bi-convex geometry imposes a corresponding concave deformation of the soft-tissues underlying the soft-tissue deforming member 7, and thus maximally restricts the microcirculation preferably at the site of fracture. While excellent results have been obtained using a soft-tissue deforming member having the above-described geometrical characteristic, it is believed that further investigation is required in order to determine exact geometrical specifications for the soft-tissue deforming member which maximize the benefits obtainable from the orthopaedic device of the present invention.

Referring to FIGS. 11, 11A, 11B and 11C in particlar, another embodiment of the method and apparatus of the present invention will now be described below.

Figure 11:
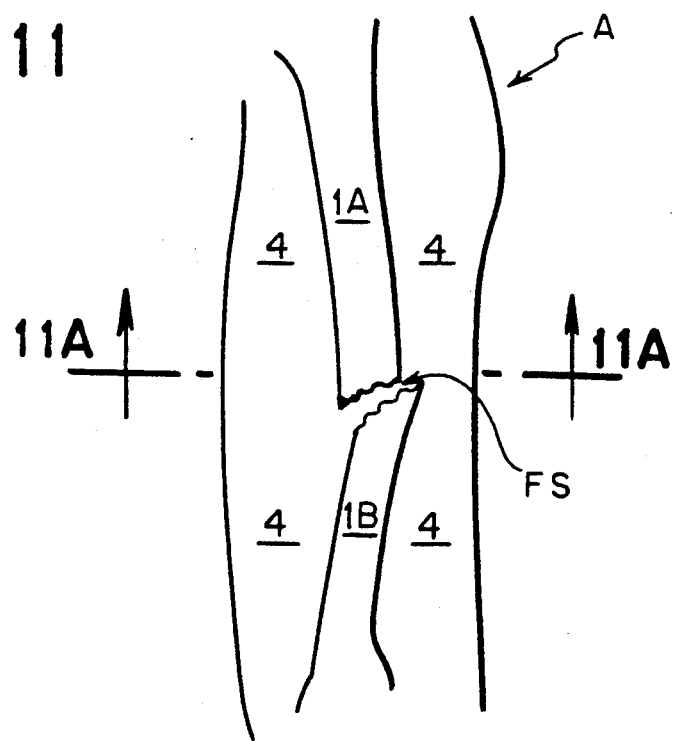
FIG. 11 shows a schematic illustration of a longitudinal sectional view in the coronal plane, of a fractured humerus showing the gross relationship between the soft-tissues and the fractured humerus shifted in direction towards a wound or vital structure.
Figure 11A:
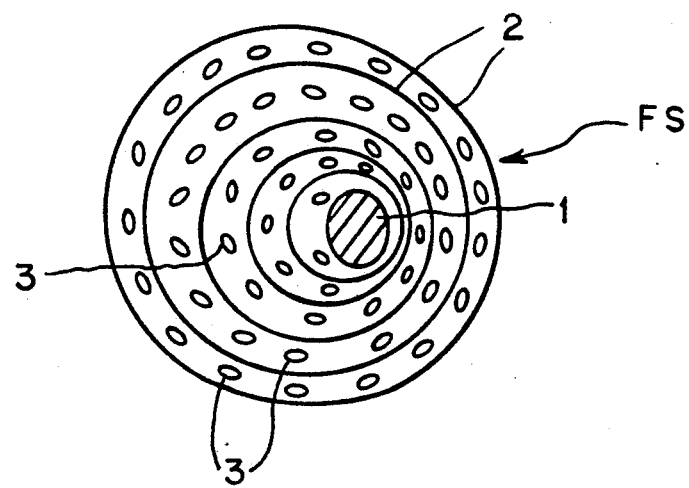
FIG. 11A is a schematic illustration of a cross section of the arm illustrated in FIG. 11 taken along line 11A—11A in the plane of the fracture site, showing a shift in the position of the humerus with respect to the soft-tissues surrounding the same and a minimally changed distribution of venous and arterial microcirculation surrounding the fracture, as illustrated in FIG. 2A, with the shift of the fractured humerus being in the direction of the wound or vital structure.

In FIG. 11, a longitudinal sectional view of an upper portion of an arm containing an angulated fractured humerus is schematically illustrated, in which adjacent the apex of the angulated fracture, a wound is present, as typically will be the case during a fracture. In such a case, applying the method described hereinbefore with respect to the fractures represented in FIGS. 3, 3A, 4 and 4A, would result in greater pain and suffering or neural dysfunction to the patient due to the necessary deformation of soft-tissues 4 between the soft-tissue deforming member 7 and the fracture site. Thus, in an alternative embodiment of the method of the present invention, the necessary (i) force distribution required in the direction of the apex of the angulated fracture and (ii) soft-tissue deformation about the fracture site, is achieved using two soft-tissue deforming members positioned substantially within the same plane, and at about 90° from each other with respect to the fractured bone. This alternative method of fracture treatment is carried out in a manner similar to the hereinbefore described method, with some minor modifications described below.

Figure 11B:
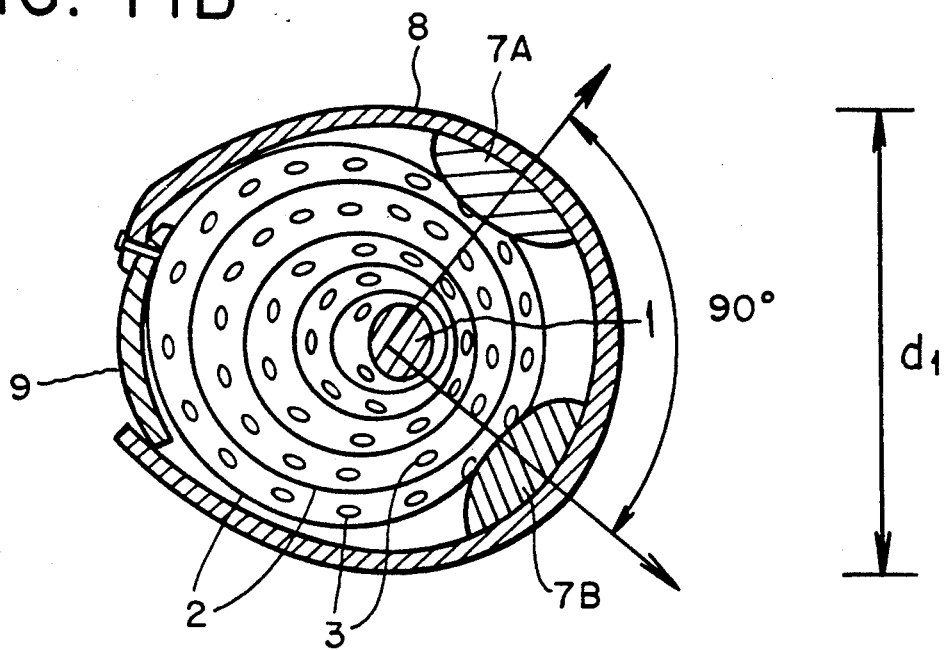
FIG. 11B is a schematic illustration of a cross section of the arm of FIG. 11, taken along line 11B—11B while a pair of soft-tissue deforming members of the device hereof are disposed along substantially perpendicular axes intersecting the fractured humerus and the arm being surrounded by the open substantially-cylindrical bracing structure of the device hereof positioning soft-tissue deforming members with respect to the fracture site and just barely contacting the skin, and avoiding the wound or vital structure.
Figure 11C:
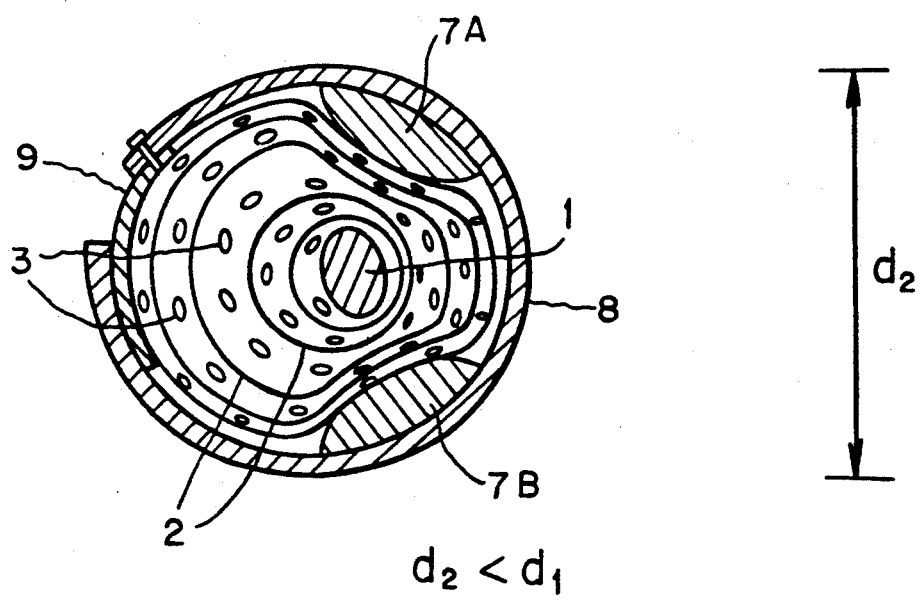
FIG. 11C is a schematic illustration of the cross-section of the arm and device hereof illustrated in FIG. 11B, in which the cross-sectional diameter of the bracing structure of the device hereof is reduced in order to produce a resultant force on the fractured humerus in a direction to reduce the angulation thereof, and altering the venous and arterial microcirculation of the soft-tissues about the fracture site, represented by a decrease in the number of open blood vessel apertures in the regions between the first and second soft-tissue deforming members and the fracture, while avoiding the wound or vital structure.

In FIG. 11B, there is shown two such soft-tissue deforming members 7A and 7B positioned at about 90° with respect to each other, with respect to the fractured bone, and within substantially the same plane. The dimensions of these soft-tissue deforming members 7A and 7B are determinable in a manner similar to that described hereinabove. Without the bracing system 6 tightened to embrace the limb, the soft-tissue deforming members 7A and 7B are adjusted so as to straddle the wound or vital structure, prior to forcing the soft-tissue deforming members into the soft-tissues about the fracture site. Then, after adjustment of the soft-tissue deforming members 7A and 7B about the fracture site, the cross-sectional diameter $d_1$ of the bracing system 6 is reduced to diameter $d_2$, using for example, the strapping mechanism 12A and 12B. As a result, the soft-tissue deforming members 7A and 7B deform the soft-tissues 4 defined generally between the members 7A and 7B and the fracture zone as illustrated in FIG. 11C, without contacting the soft-tissues in the region of the wound or vital structure. In addition, three point fixation of pressure to the angulated fracture is achieved to reduce the angulation as described in detail with respect to the embodiment described hereinbefore using single soft-tissue deforming member 7. Notably, within the scope and spirit of the present invention, soft-tissue deforming members 7A and 7B may also be disposed at angles other than 90° in a particular plane in order to synthesize a force distribution sufficient to carry out the fracture treatment method of the present invention.

Also, in particular cases, a long bone fracture may have undergone angulation in both the coronal and sagittal planes, thus necessitating that the soft-tissue deforming members be positioned in different cross-sectional planes along the longitudinal direction of the fractured long bone. In such cases, more complicated arrangements of the soft-tissue deforming members are typically required, as can be appreciated by the illustrations provided in FIGS. 12 through 12F and discussion below.

Figure 12:
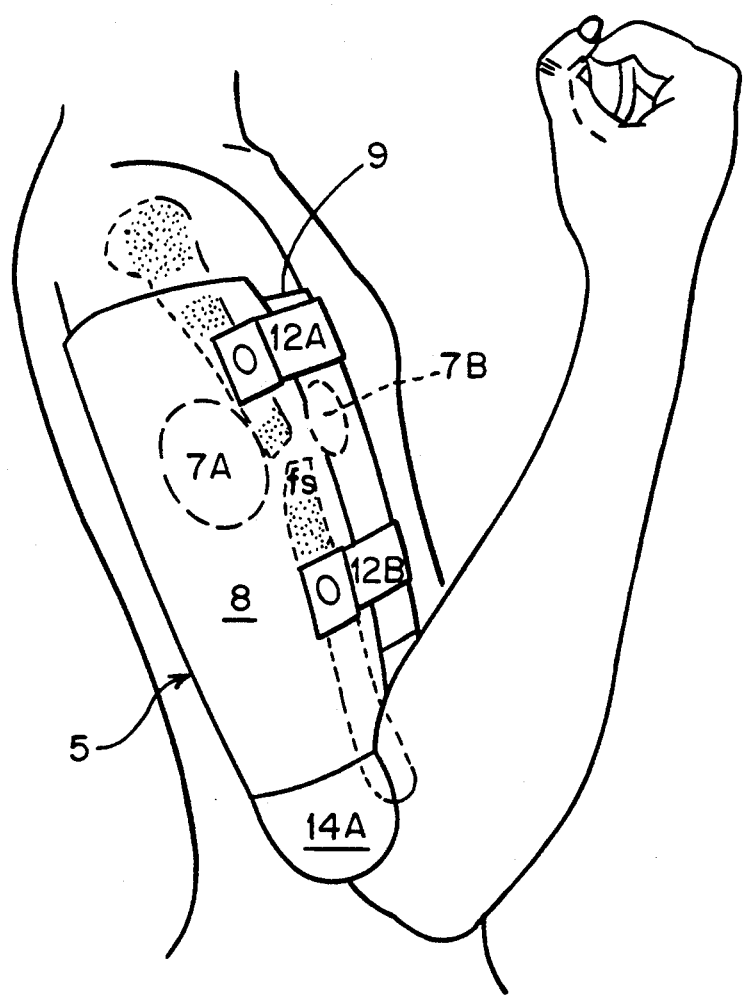
FIG. 12 is a schematic illustration of a perspective view of an arm containing a diaphyseal fracture in the humerus, in which there is shown the open substantially-cylindrical bracing structure of the device of the present invention, which surrounds the fractured humerus and a pair of soft-tissue deforming members are disposed respectively in perpendicular planes with respect to the apex of the fracture, and in substantially the same cross-sectional plane.
Figure 12B:
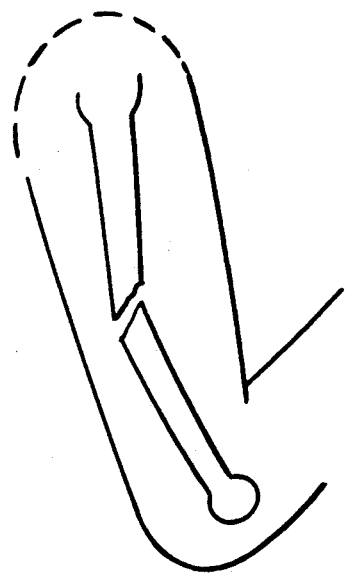
FIG. 12B is a schematic illustration of a longitudinal cross-sectional view of the arm in the sagittal plane, showing the gross relationship between the soft-tissues and the fractured hunerus, also shifted in the posterior direction.
Figure 12A:
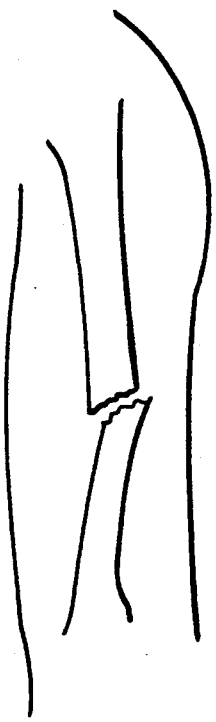
FIG. 12A is a schematic illustration of a longitudinal cross-sectional view of the arm in the coronal plane, showing the gross relationship between the soft-tissue and the fractured humerus shifted in the lateral direction.

In the schematic illustration of FIG. 12, there is shown an arm with the orthopaedic device 5 of the present invention applied thereto. This arm has a humerus with a fracture angulated in both the coronal and sagittal planes, illustrated in FIGS. 12A and 12B, respectively. Such types of fractures shall hereinafter be referred to as fractures having "angulations" in an oblique plane.

Figure 12D:
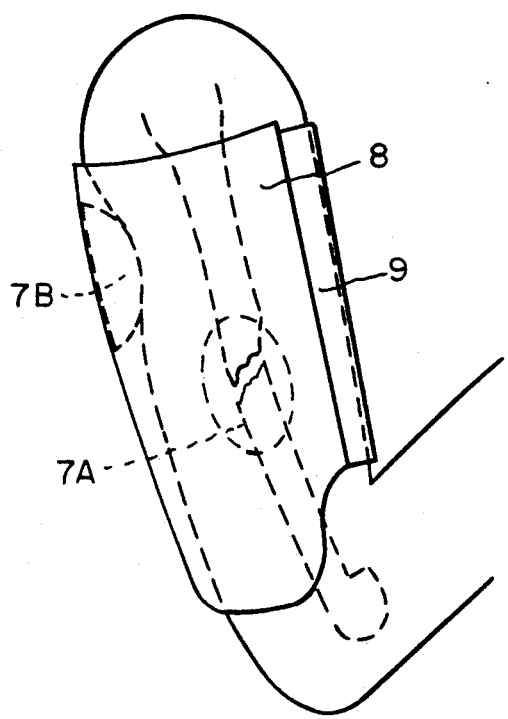
FIG. 12D is a schematic illustration of a longitudinal cross-sectional view in the sagittal plane, of the arm in FIGS. 12A and 12B, showing a reduction in the angulated humeral fracture, using two soft-tissue deforming members disposed in different cross-sectional planes of the arm.
Figure 12C:
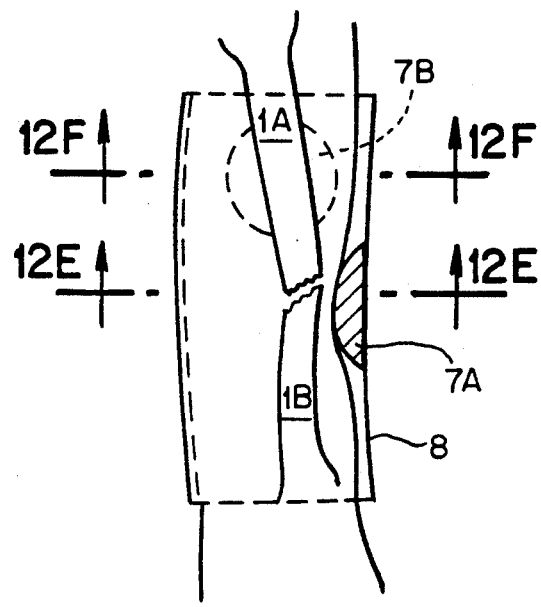
FIG. 12C shows a schematic illustration of a longitudinal sectional view in the coronal plane, of the arm of FIGS. 12A and 12B, showing a reduction in the angulated humeral fracture, using two soft-tissue deforming members, each of which lies in a different cross-sectional plane of the arm, and disposed in different longitudinal planes which pass through the humerus and being surrounded by the open-bracing structure of the device hereof positioning the soft-tissue deforming member to reduce the fracture.

In particular, FIG. 12C illustrates the placement or strategic positioning of a soft-tissue deforming member 7A with respect to the fracture site along a first cross-sectional plane, so as to reduce the angulation of the fracture in the coronal plane. FIG. 12D illustrates the placement of a soft-tissue deforming member 7B with respect to the fracture site along a second cross-sectional plane, so as to reduce the angulation of the fracture along the sagittal direction. Using this configuration of soft-tissue deforming members in the bracing system 6 of the present invention, reduction of angulation of fractures in the oblique plane can be achieved while realizing the "beneficial effects" of the method and apparatus of the present invention. Notably, however, in this particular configuration, soft-tissue deforming member 7B will not be operative in achieving the beneficial biochemical effects described hereinbefore, while soft-tissue deforming member 7A will be.

Figure 12E:
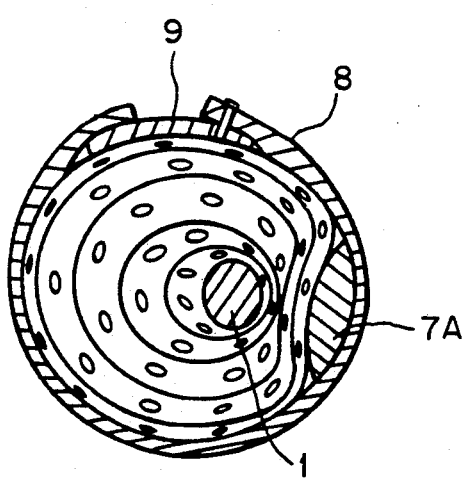
FIG. 12E is a schematic illustration of a cross-sectional view of the arm illustrated in FIG. 12C, taken along line 12E—12E, showing a relative shift in the position of the humerus with respect to the soft-tissues surrounding the same, and a grossly altered distribution of venous and arterial microcirculation surrounding the fracture, represented by a decrease in the number of open blood vessel apertures in the region between the soft-tissue deforming member and the fracture.
Figure 12F:
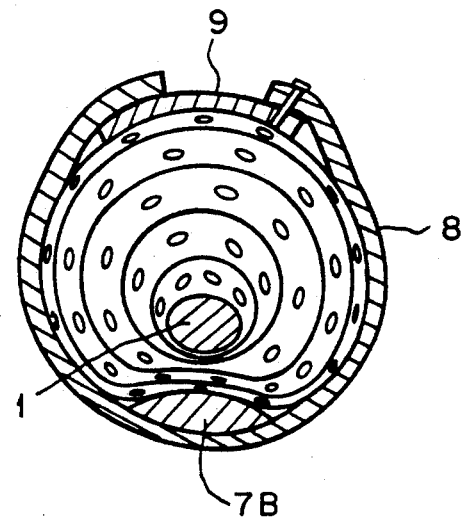
FIG. 12F is a schematic illustration of a cross-sectional view of the arm illustrated in FIG. 12C taken along line 12F—12F, showing a relative shift in the position of the humerus with respect to the soft-tissues surrounding the same, and a grossly altered distribution of venous and arterial microcirculation in the locale of the unbroken shaft of the proximal humerus, represented by a decrease in the number of open blood vessel apertures in the region between the soft-tissue deforming member and the humeral shaft.

In FIGS. 12E and 12F, respectively, cross-sectional views taken along lines 12E—12E and 12F—12F of FIG. 12C illustrate the deforming of soft-tissues and relative shifting of bone fragments in a manner similar to that described in connection with the other embodiments of the present invention hereinbefore described.

In particular cases, when the fracture has occurred at the end of a long bone or when an internal fixation device has been used, the orthopaedic device of the present invention may not be as effective in providing the stress distribution to reduce the fracture, or it may not be needed to do so. It may still be used to tamponade the torn blood vessels at the fracture site and achieve the beneficial biochemical effects described hereinbefore.

Referring now to FIGS. 8A and 8B, 9A and 9B, and 10A and 10B, empirical results of the method and orthopaedic device of the present invention will now be discussed.

Figure 8A:
FIG. 8A shows an X-ray image (i.e. roentgenogram) in the anterior-posterior (AP) projection, of an angulated fractured humerus taken prior to treatment.
Figure 8B:
FIG. 8B is an X-ray image in a lateral projection, of the angulated fractured humerus shown in FIGS. 7A and 7B, illustrating its angulation and gross displacement with loss of bony contact at the fracture site.

The X-ray images of FIGS. 8A and 8B illustrate the condition of an actual humerus with an angulated fracture, after having been conventionally treated for about one week in a conventional plaster of paris splint. Notably, using such a conventional method and apparatus of fracture treatment, there remained, while in the splint, substantial angulation of the fractured humerus and gross displacement, with loss of bony contact at the fracture site.

Figure 9B:
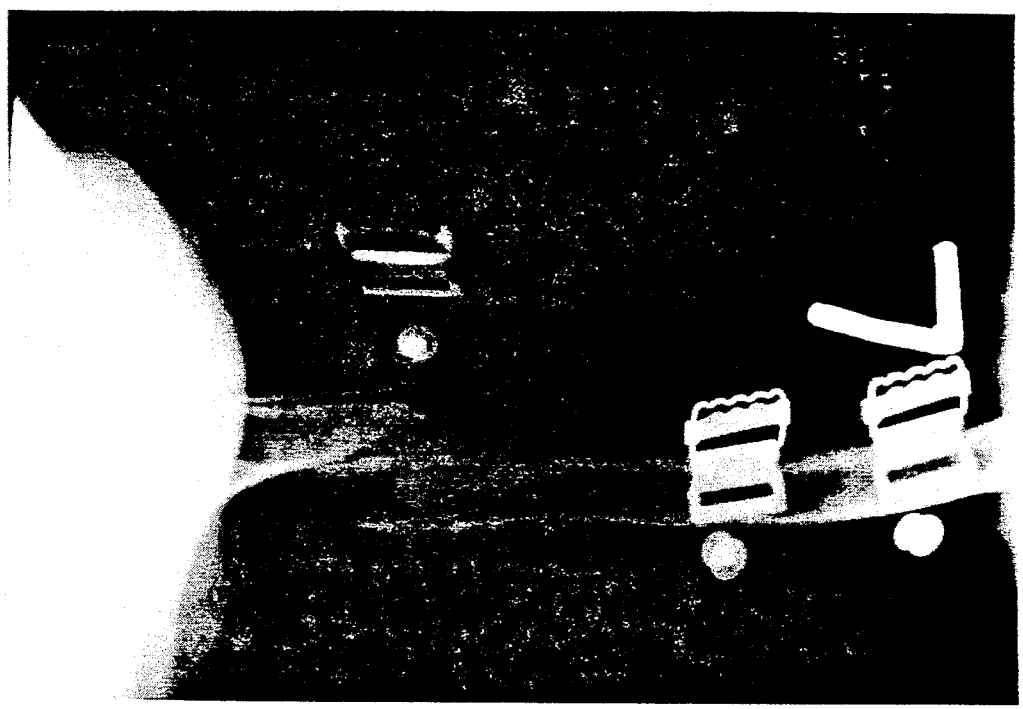
FIG. 9B shows an X-ray image in the lateral projection, of the fractured humerus illustrated in FIGS. 8A and 8B, while being reduced in and encircled by the orthopaedic device of the present invention, showing (i) the reduction of the gross displacement and the bony contact at the fracture site, and (ii) position of the soft-tissue deforming member relative to the fracture site.
Figure 9A:
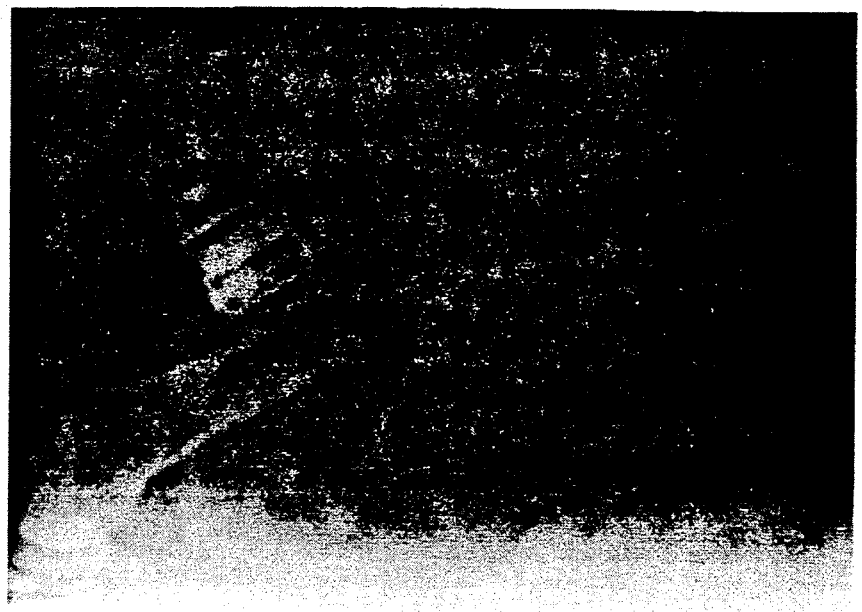
FIG. 9A shows an X-ray image in the AP projection, of the fractured humerus illustrated in FIGS. 8A and 8B, while being reduced in and encircled by the orthopaedic device of the present invention, showing the position of the soft-tissue deforming member relative to the fracture site.

After removing the splint from the arm of FIGS. 8A and 8B and applying the method and orthopaedic device 5 of the present invention, the X-ray images of FIGS. 9A and 9B were taken. These X-ray images clearly show a marked reduction in the gross displacement and establishment of bony contact at the fracture site.

Figure 10B:
FIG. 10B shows an X-ray image in the lateral projection, of the healed fractured humerus illustrated in FIGS. 8A, 8B, 9A and 9B, having an acceptable reduction, and massive callous formation.
Figure 10A:
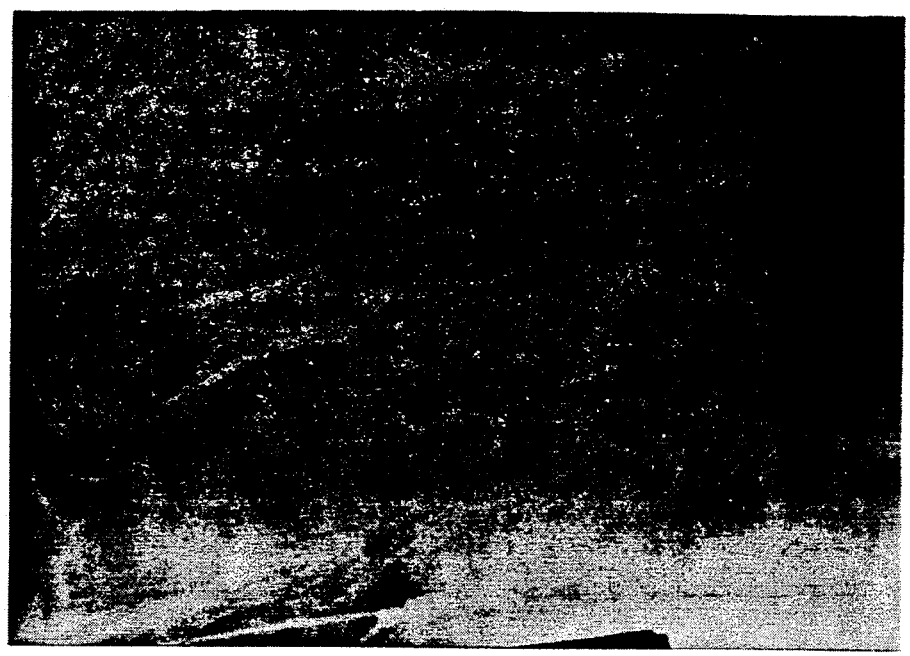
FIG. 10A shows an X-ray image in the AP projection, of the healed fractured humerus illustrated in FIGS. 8A, 8B, 9A and 9B, having essentially perfect alignment and massive callous formation.

After about 8 weeks of treatment using the method and orthopaedic device 5 of the present invention, X-ray images of FIGS. 10A and 10B were taken. These X-ray images show the healed fractured humerus, having essentially perfect alignment in the AP projection, acceptable reduction in the lateral projection, with massive callous formation. Notably, after only several days after the orthopaedic device 5 hereof was applied to the extremity, the patient was able to exercise the extremity, and expressed a marked mitigation of pain.

Figure 13B:
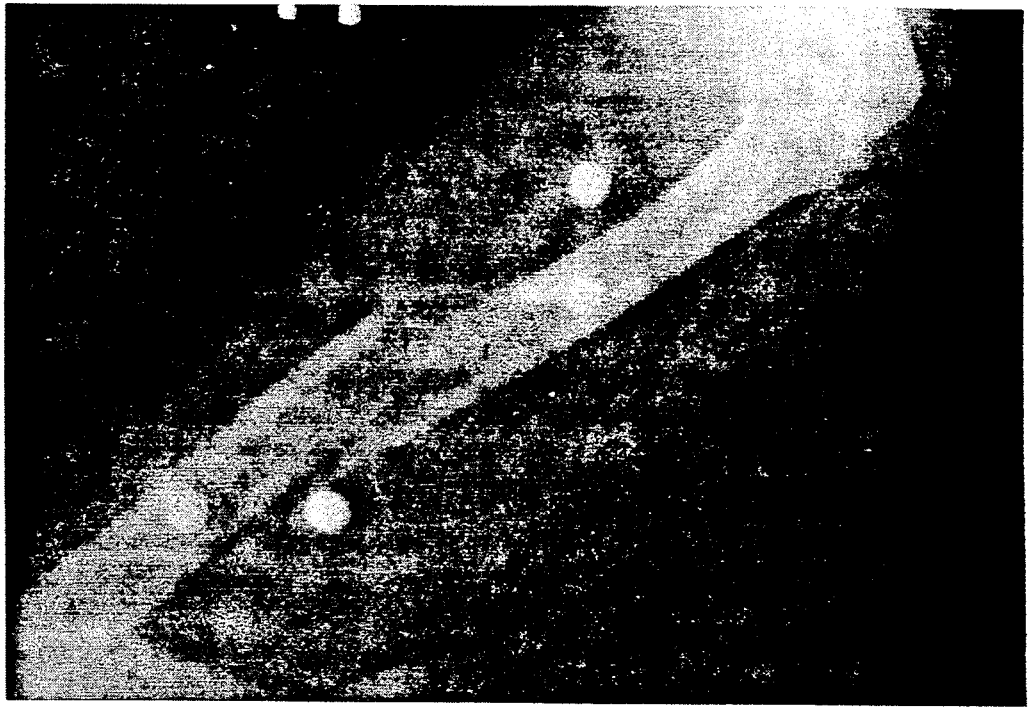
FIG. 13B is an X-ray image in a lateral projection, of an arm having an anteriorly angulated diaphyseal fracture of the humerus of FIG. 13A, with the orthopaedic device of the present invention applied thereto.
Figure 13A:
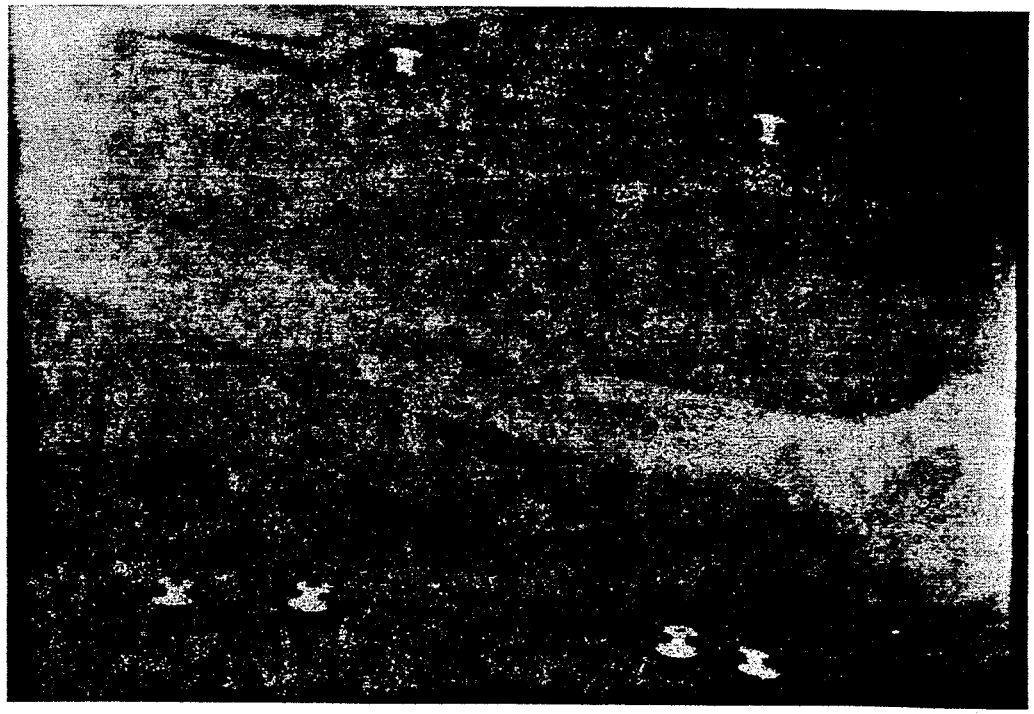
FIG. 13A is an X-ray image in an anterior-posterior projection, of an arm having an angulated diaphyseal fracture of the humerus, with the orthopaedic device of the present invention applied thereto.

In FIGS. 13A and 13B, there are also shown X-ray images of another angulated fractured humerus, taken in the A-P and lateral views, while embraced within the orthopaedic device 5 of the present invention for about 10 days. Notably, in this particular application, the soft-tissue deforming members have been embedded with wires in order to render the soft-tissue deforming members radio-opaque and illustrate the corresponding deformation caused to the soft-tissues while the orthopaedic device 5 is applied to the arm during treatment.

While the method and apparatus of the present invention has been described above in connection with a humeral fracture, the orthopaedic device and methodology hereof has been found to provide excellent results in connection with angulated femoral fractures, a modification in the treatment program is, however, necessary.

In particular, with femoral fractures, modification in the fracture treatment program includes a short period of tibial pin traction along with the use of the orthopaedic device of the present invention. However, the traction forces needed are much less compared to what is required using more conventional techniques. Notably, this allows the fracture to impact and consolidate earlier. The orthopaedic device of the present invention applied to fracture femurs, also provides dramatic pain relief which thereby allows the patient to move about in bed and exercise the extremity within a short time after its application.

Well known in the art, mechanical evidence of fracture healing is the ability of a patient to perform a straight leg raise with traction forces removed and the orthopaedic device hereof remaining in place. Together with radiological evidence of healing, this sign indicates the patient may begin to ambulate. At that time, when the patient may begin to ambulate, the orthopaedic device for the fractured femur can be extended into a long leg brace with a fixed or flexible knee hinge. In this manner, the patient may thus continue to benefit from the three-point fixation of the fractured femur provided by the orthopaedic device, in order to maintain the fracture fragment in alignment as weight bearing is initiated.

While the particular embodiments shown and described above have proven to be useful in many applications involving the orthopaedic arts, further modifications herein disclosed will occur to persons skilled in the art to which the present invention pertains and also such modifications are deemed to be within the scope and spirit of the present invention defined by the appended claims.

What is claimed is:

1. A method of treating a fracture in a long bone, to aid in reducing the angulation of said fracture and/or to stimulate healing of said fracture, said method comprising the steps of:

(a) in a limb containing an angulated fracture in a long bone surrounded by soft-tissues which have a venous and/or arterial microcirculation of blood, disposing at least one soft-tissue deforming member in proximity with said fracture,
wherein said soft-tissue deforming member has a predetermined three-dimensional geometry having length, width and height dimensions, and said limb at said fracture site has a diameter;

(b) specifying said height of said soft-tissue deforming member in terms of a constant K defined as the ratio of said height to said diameter, where K lies in the range of about 0.05 to about 0.25,
wherein said height specification step comprises:
(1) selecting an initial uncompressed height $h_{uc}$ for said soft-tissue deforming member, on the basis of said constant K and the circumference of said limb at said fracture site;
(2) applying said soft-tissue deforming member specified in substep (1) to said limb, and reducing a cross-sectional dimension of bracing structure so as to cause said soft-tissue deforming member to deform said soft-tissues and undergo compression;
(3) forming an image of said limb and said soft-tissue deforming member;
(4) from said image formed in step (3), measuring the compressed height $h_c'$ of said soft-tissue deforming member;
(5) from said image, computing the compressed height $h_c$ of said soft-tissue deforming member, on the basis of (a) the measured compressed diameter of said limb at said fracture site and (b) said constant K;
(6) comparing said measured compressed height $h_c'$ and said computed height $h_c$, and on the basis of such comparison, angulation reduction considerations, and soft-tissue necrosis considerations, changing the height dimension of said soft-tissue deforming member; and
(7) repeating substeps (2) through (6), until acceptable reduction of said angulated fracture is achieved.

2. A method of treating a fracture in a long bone, to aid in reducing the angulation of said fracture and/or to stimulate healing of said fracture, said method comprising the steps of:

(a) in a limb containing an angulated fracture in a long bone surrounded by soft-tissue which have a venous and/or arterial microcirculation of blood, disposing at least one soft-tissue deforming member in proximity with said fracture,
wherein said soft-tissue deforming member has a predetermined three-dimensional geometry having length, width and height dimensions, and said limb at said fracture site has a diameter;

(b) specifying said height of said soft-tissue deforming member in terms of a constant K defined as the ratio of said height to said diameter, where K lies in the range of about 0.05 to about 0.25,
wherein said height specification step comprises:
(1) selecting an initial uncompressed height $h_{uc}$ for said soft-tissue deforming member, on the basis of said constant K and the circumference of said limb at said fracture site;
(2) applying to said limb, said soft-tissue deforming member specified in substep (1), and reducing a cross-sectional dimension of a bracing structure so as to cause said soft-tissue deforming member to deform said soft-tissues, and undergo compression;
(3) forming an image of said limb and said soft-tissue deforming member;
(4) from said image formed in step (3), measuring the compressed height $h_c'$ of said soft-tissue deforming member;
(5) from said image, computing the compressed height $h_c$ of said soft-tissue deforming member, on the basis of (a) the measured compressed diameter of said limb at said fracture site and (b) said constant K;
(6) comparing said measured compressed height $h_c'$ and said computed height $h_c$, and on the basis of such comparison, angulation reduction considerations, and soft-tissue necrosis considerations, changing the height dimension of said soft-tissue deforming member; and
(7) On the basis of said comparison made in substep (6),
(A) determining the value of said ratio $K'$ for said limb, and
(B) comparing said ratio $K'$ with said ratio K, so as to obtain a measure indicative of the care to be exercised in changing said soft-tissue deforming member during the reiteration of substeps (2) through (6);
(8) repeating substeps (2) through (6), until acceptable reduction of said angulation fracture is achieved.

3. A method of treating fractures in a long bone, to aid in reducing the angulation of said fracture and to physically tamponade torn blood vessels at a fracture site and reduce bleeding therefrom, said method comprising the steps of:
(a) in a limb containing an angulated fracture in a long bone surrounded by soft-tissues which have a venous and/or arterial microcirculation of blood including blood vessels which are torn and bleeding at the fracture site, disposing at least one soft-tissue deforming member in proximity with said fracture,
wherein said soft-tissue deforming member has a predetermined three-dimensional geometry having length, width and height dimensions, and said limb at said fracture site has a diameter;
(b) specifying said height of said soft-tissue deforming member in terms of a constant K defined as the ratio of said height to said diameter, where K lies in the range of about 0.05 to about 0.25 wherein said height specification step comprises:
(1) selecting an initial uncompressed height $h_{uc}$ for said soft-tissue deforming member, on the basis of said constant K and the circumference of said limb at said fracture site;
(2) applying to said limb, said soft-tissue deforming member specified in substep (1), and reducing said cross-sectional dimension of said bracing structure so as to cause said soft-tissue deforming member to deform said soft-tissues, and said soft-tissue deforming member undergoes compression;
(3) forming an image of said limb and said soft-tissue deforming member;
(4) from said image formed in step (3), measuring the compressed height $h_c'$ of said soft-tissue deforming member;
(5) from said image, computing the compressed height $h_c$ of said soft-tissue deforming member, on the basis of (a) the measured compressed diameter of said limb at said fracture site and (b) said constant K;
(6) comparing said measured compressed height $h_c'$ and said computed height $h_c$, and on the basis of such comparison, angulation reduction considerations, and soft-tissue necrosis considerations, changing the height dimension of said soft-tissue deforming member; and
(7) repeating substeps (2) through 6), until acceptable reduction of said angulated fracture is achieved.

4. An orthopaedic device for treating fractures in a long bone of a limb, comprising:
(a) a bracing structure for encircling a limb having a fracture of its long bone, said bracing structure is substantially rigid along its longitudinal dimension substantially parallel to the limb and is of a suitable length and circumference for encircling and laterally supporting said limb, said bracing structure having a longitudinal opening to allow the orthopaedic device to be applied to the limb, and a selectively adjustable cross-sectional dimension;
(b) a substantially rigid, soft tissue deforming member having a convex surface which does not conform to the shape of the limb, for contacting and applying an uneven pressure distribution at the interface of the convex surface and said soft tissue, said soft tissue deforming member being attached on a side opposite said convex surface to an interior surface of said bracing structure; and
(c) means for reducing the cross-sectional dimension of said bracing structure to urge the convex surface of said soft tissue deforming member against said limb causing an uneven pressure distribution at the interface of the convex surface and said soft tissue, and deformation of the soft tissue between said soft tissue deforming member and said fracture of said long bone, and urging said limb against the inner surface of said bracing structure to intimately hold and support the soft tissue of the limb.

5. An Orthopaedic device as recited in claim 4, wherein said soft tissue deforming member is detachably disposed on the inner surface of said bracing structure.

6. An orthopaedic device as recited in claim 4, wherein said bracing structure is substantially rigid to bending and torsional moments along its transverse direction.

7. An orthopaedic device as recited in claim 4, further comprising a tongue-shaped structure which is flexibly connected to said bracing structure for placement within said longitudinal opening of said bracing structure.

8. An orthopaedic device as recited in claim 5, further including more than one of said soft tissue deforming member.

9. An orthopaedic device as recited in claim 5, wherein said soft tissue deforming member is detachably disposed on the inner surface of said bracing structure by means of a loop and hook attachment means between said side opposite said convex surface of said soft tissue deforming member and said inner surface of said bracing structure.

10. An orthopaedic device as recited in claim 7, wherein said tongue-shaped structure is detachably connected to said bracing structure by means of a loop and hook attachment means between said inner surface of said bracing structure and an outer surface of said tongue-shaped structure.

11. An orthopaedic device as recited in claim 4, wherein said means for reducing the cross-sectional dimension of said bracing structure comprises strapping means, said strapping means connected at one end to a surface of said bracing structure on one side of said longitudinal opening, and another end of said strapping means being selectively attachable to another side of said longitudinal opening of said bracing structure to selectively reduce the said cross-sectional dimension of said bracing structure.

12. An orthopaedic device as recited in claim 4, wherein said soft tissue deforming member has a biconvex surface.

13. An orthopaedic device as recited in claim 4, wherein the distance between said convex surface of said soft tissue deforming member and said side opposite said convex surface, defined as the height of said soft tissue deforming member, whereby a ratio of said height to a diameter of said limb measured at the fracture, is in the range of from about 0.05 to about 0.25.

14. An orthopaedic device as recited in claim 6, further comprising anti-torsion means disposed at one end of said bracing structure for preventing the transmission of torsional moments to said bracing structure.

15. A method of treating a fracture in a long bone of a limb to aid in reducing the angulation of the fracture and stimulate healing, the method comprising:
(a) applying an orthopaedic device to a limb having a fracture of its long bone, through a longitudinal opening of a bracing structure of said orthopaedic device to encircle said limb with the bracing structure, said bracing structure is substantially rigid along its longitudinal dimension substantially parallel to the limb and is of a suitable length and circumference to encircle and laterally support the limb and has a selectively adjustable cross-sectional dimension;
(b) contacting a convex surface of a substantially rigid, soft tissue deforming member against the limb, said convex surface does not conform to the shape of the limb and is configured for contacting and applying in an uneven pressure distribution at the interface of the convex surface and the soft tissue of said limb, said soft tissue deforming member being attached on the side opposite said convex surface to an interior surface of said bracing structure; and
(c) reducing the cross-sectional dimensional of said bracing structure to urge the convex surface of said soft tissue deforming member against said limb, thereby causing an uneven pressure distribution at the interface of the convex surface and said soft tissue, and deformation of the soft tissue between said soft tissue deforming member and said fracture of said long bone, and urging said limb against the inner surface of said bracing structure to intimately hold and support the soft tissue of the limb, whereby said uneven pressure distribution at the interface of the convex surface and said soft tissue causes deformation of the soft tissue between said soft tissue deforming member and said fracture of said long bone, inhibits the venus and/or arterial microcirculation of blood about said fracture, aids in reducing angulation of the fracture and stimulates healing of the fracture.

16. A method as recited in claim 5, further comprising detaching said soft tissue deforming member from its original position, and reattaching said soft tissue deforming member in another position on said interior surface of said bracing structure to place said convex surface of said soft tissue deforming member against said soft tissue at a more desired position in relation to the fracture of said long bone.

17. A method as recited in claim 15, further comprising placing more than one of said soft tissue deforming members against said soft tissue of the limb having a fractured long bone, to cause deformation of the soft tissue between said soft tissue deforming members and said fracture of said long bone.

18. A method of stimulating an enchondral osteogenesis reaction at the site of a fracture in a long bone of a limb having layers of soft tissue with venus and/or arterial microcirculation of blood in the soft tissue, the method comprising:
(a) applying an orthopaedic device to a limb having a fracture of its long bone, through a longitudinal opening of a bracing structure of said orthopaedic device to encircle said limb with the bracing structure, said bracing structure is substantially rigid along its longitudinal dimension substantially parallel to the limb and is of a suitable length and circumference to encircle and laterally support the limb and has a selectively adjustable cross-sectional dimension;
(b) contacting a convex surface of a substantially rigid, soft tissue deforming member against the limb, said convex surface does not conform to the shape of the limb and is configured for contacting and applying in an uneven pressure distribution at the interface of the convex surface and the soft tissue of said limb, said soft tissue deforming member being attached on the side opposite said convex surface to an interior surface of said bracing structure; and
(c) reducing the cross-sectional dimensional of said bracing structure to urge the convex surface of said soft tissue deforming member against said limb, thereby causing an uneven pressure distribution at the interface of the convex surface and said soft tissue, and deformation of the soft tissue between said soft tissue deforming member and said fracture of said long bone, and urging said limb against the inner surface of said bracing structure to intimately hold and support the soft tissue of the limb, whereby the venus and/or arterial microcirculation of blood in said soft tissue is restricted about said fracture site in response to said uneven pressure distribution, thereby stimulating the enchondral osteogenesis reaction at the fracture site.

19. A method as recited in claim 18, further comprising detaching said soft tissue deforming member from its original position, and reattaching said soft tissue deforming member in another position on said interior surface of said bracing structure to place said convex surface of said soft tissue deforming member against said soft tissue at a more desired position in relation to the fracture of said long bone.

20. A method as recited in claim 18, further comprising placing more than one of said soft tissue deforming members against said soft tissue of the limb having a fractured long bone, to cause deformation of the soft tissue between said soft tissue deforming members and said fracture of said long bone.

21. A method of mitigating pain associated with a fracture of a long bone which is experienced by a patient, said long bone is surrounded by soft tissue including periosteal tissue, muscle and fascial tissue having a microcirculation of blood in said soft tissue and having pain sensory receptors including free pain nerve endings, all of which are in intimate communication with an interstitial fluid environment of the soft tissue having a characteristic pH and containing elemental minerals including calcium in a bound and free ionic state, the sensory receptors are activated by various mechanical stimuli and their excitability is responsive to free calcium ion concentration, the Ph of the interstitial fluid is controlled on the basis of a balance between cellular metabolism and blood transport through said microcirculation of blood in the soft tissues, the method comprising:
  (a) applying an orthopaedic device to a limb having a fracture of its long bone, through a longitudinal opening of a bracing structure of said orthopaedic device to encircle said limb with the bracing structure, said bracing structure is substantially rigid along its longitudinal dimension substantially parallel to the limb and is of a suitable length and circumference to encircle and laterally support the limb and has a selectively adjustable cross-sectional dimension;
  (b) contacting a convex surface of a substantially rigid, soft tissue deforming member against the limb, said convex surface does not conform to the shape of the limb and is configured for contacting and applying in an uneven pressure distribution at the interface of the convex surface and the soft tissue of said limb, said soft tissue deforming member being attached on the side opposite said convex surface to an interior surface of said bracing structure; and
  (c) reducing the cross-sectional dimensional of said bracing structure to urge the convex surface of said soft tissue deforming member against said limb, thereby causing an uneven pressure distribution at the interface of the convex surface and said soft tissue, and deformation of the soft tissue being said soft tissue deforming member and said fracture of said long bone, and urging said limb against the inner surface of said bracing structure to intimately hold and support the soft tissue of the limb, whereby the pH of said interstitial fluid is decreased and the free calcium ion concentration of the interstitial fluid is increased thereby diminishing the excitability of the pain sensory receptors including the free pain nerve endings which are in intimate communication with said interstitial fluid so that the pain associated with a fracture of the long bone which is experienced by a patient is mitigated.

22. A method as recited in claim 21, further comprising detaching said soft tissue deforming member from its original position, and reattaching said soft tissue deforming member in another position on said interior surface of said bracing structure to place said convex surface of said soft tissue deforming member against said soft tissue at a more desired position in relation to the fracture of said long bone.

23. A method as recited in claim 21, further comprising placing more than one of said soft tissue deforming members against said soft tissue of the limb having a fractured long bone, to cause deformation of the soft tissue between said soft tissue deforming members and said fracture of said long bone.

24. A method of enhancing coagulation reactions at a fracture of a long bone and hasten the formation of a fracture clot, said long bone being surrounded by soft tissue including periosteal tissue, muscle and fascial tissue, said soft tissue having a microcirculation of blood, including blood cells and blood coagulation factors which function in a cascade mechanism for blood coagulation characterized by a plurality of coagulation reactions, said soft tissue including said periosteal tissue, muscle and fascial tissues being in intimate communication with an interstitial fluid environment of said soft tissue having a characteristic pH and containing elemental minerals including calcium in a bound and free ionic state, said pH of the interstitial fluid is controlled on the basis of the balance between cellular metabolism and blood transport through the microcirculation of blood in the soft tissue, the method comprising: p1 (a) applying an orthopaedic device to a limb having a fracture of its long bone, through a longitudinal opening of a bracing structure of said orthopaedic device to encircle said limb with the bracing structure, said bracing structure is substantially rigid along its longitudinal dimension substantially parallel to the limb and is of a suitable length and circumference to encircle and laterally support the limb and has a selectively adjustable cross-sectional dimension;
  (b) contacting a convex surface of a substantially rigid, soft tissue deforming member against the limb, said convex surface does not conform to the shape of the limb and is configured for contacting and applying in an uneven pressure distribution at the interface of the convex surface and the soft tissue of said limb, said soft tissue deforming member being attached on the side opposite said convex surface to an interior surface of said bracing structure; and
  (c) reducing the cross-sectional dimensional of said bracing structure to urge the convex surface of said soft tissue deforming member against said limb, thereby causing an uneven pressure distribution at the interface of the convex surface and said soft tissue, and deformation of the soft tissue between said soft tissue deforming member and said fracture of said long bone, and urging said limb against the inner surface of said bracing structure to intimately hold and support the soft tissue of the limb, whereby the pH of said interstitial fluid is decreased in response to said uneven pressure distribution at the interface of the convex surface and said soft tissue which restricts said microcirculation of blood in said soft tissue, said decrease of pH increases the free calcium ion concentration of said interstitial fluid and accelerates one or more of said coagulation reactions, thereby increasing the speed of formation of said fracture clot at said fracture.

25. A method as recited in claim 24, further comprising detaching said soft tissue deforming member from its original position, and reattaching said soft tissue deforming member in another position on said interior surface of said bracing structure to place said convex surface of said soft tissue deforming member against said soft tissue at a more desired position in relation to the fracture of said long bone.

26. A method as recited in claim 24, further comprising placing more than one of said soft tissue deforming members against said soft tissue of the limb having a fractured long bone, to cause deformation of the soft tissue between said soft tissue deforming members and said fracture of said long bone.

27. A method of treating a fracture in a long bone and aid in reducing the angulation of said fracture and physically tamponade torn blood vessels at the site of the fracture and reduce bleeding from said torn blood vessels, the method comprising:
   (a) applying an orthopaedic device to a limb having a fracture of its long bone, through a longitudinal opening of a bracing structure of said orthopaedic device to encircle said limb with the bracing structure, said bracing structure is substantially rigid along its longitudinal dimension substantially parallel to the limb and is of a suitable length and circumference to encircle and laterally support the limb and has a selectively adjustable cross-sectional dimension;
   (b) contacting a convex surface of a substantially rigid, soft tissue deforming member against the limb, said convex surface does not conform to the shape of the limb and is configured for contacting and applying in an uneven pressure distribution at the interface of the convex surface and the soft tissue of said limb, said soft tissue deforming member being attached on the side opposite said convex surface to an interior surface of said bracing structure; and
   (c) reducing the cross-sectional dimensional of said bracing structure to urge the convex surface of said soft tissue deforming member against said limb, thereby causing an uneven pressure distribution at the interface of the convex surface and said soft tissue, and deformation of the soft tissue between said soft tissue deforming member and said fracture of said long bone, and urging said limb against the inner surface of said bracing structure to intimately hold and support the soft tissue of the limb,
   wherein the uneven pressure distribution at the interface of the convex surface of said soft tissue deforming member and said soft tissue of said limb physically tamponades torn blood vessels at said fracture site and reduces the bleeding from said torn blood vessels.

28. A method as recited in claim 27, further comprising detaching said soft tissue deforming member from its original position, and reattaching said soft tissue deforming member in another position on said interior surface of said bracing structure to place said convex surface of said soft tissue deforming member against said soft tissue at a more desired position in relation to the fracture of said long bone.

29. A method as recited in claim 27, further comprising placing more than one of said soft tissue deforming members against said soft tissue of the limb having a fractured long bone, to cause deformation of the soft tissue between said soft tissue deforming members and said fracture of said long bone.

* * * * *

UNITED STATES PATENT AND TRADEMARK OFFICE
CERTIFICATE OF CORRECTION

PATENT NO. : 5,171,310

DATED : December 15, 1992

INVENTOR(S) : Chisena

It is certified that error appears in the above-identified patent and that said Letters Patent is hereby corrected as shown below:

Column 11, Line 61,      "Figs. 1, IA, 2", should read --Figs. 1, 1A, 2--";

Column 14, Line 28,      "location o the", should read --location on the--;

Column 14, Lines 28-29,      "surface 22 of either n the bracing or", should read --surface 22 of either the bracing or--; and Column 17, Line 19,      "[$Ca^{++}$ in the" should read --[$Ca^{++}$] in the--.

UNITED STATES PATENT AND TRADEMARK OFFICE
CERTIFICATE OF CORRECTION

PATENT NO. : 5,171,310
DATED : December 15, 1992
INVENTOR(S) : Chisena

It is certified that error appears in the above-identified patent and that said Letters Patent is hereby corrected as shown below:

Column 29,
Claim 21, Line 51.     "tissue being said", should read --tissue between said--; and Column 30,
Claim 24, Lines 17-18    "p1 (a) applying an", should be a new paragraph,
    --(a) applying an--.

Signed and Sealed this

Seventh Day of December, 1993

BRUCE LEHMAN

Attest:

Attesting Officer     Commissioner of Patents and Trademarks